(12) United States Patent
Han

(10) Patent No.: US 7,851,148 B2
(45) Date of Patent: Dec. 14, 2010

(54) METHOD AND KIT FOR PRIMER BASED MULTIPLEX AMPLIFICATION OF NUCLEIC ACIDS EMPLOYING PRIMER BINDING TAGS

(75) Inventor: Jain Han, Huntsville, AL (US)

(73) Assignee: Qiagen GmbH, Hilden (DE)

( * ) Notice: Subject to any disclaimer, the term of this patent is extended or adjusted under 35 U.S.C. 154(b) by 1042 days.

(21) Appl. No.: 10/575,804

(22) PCT Filed: Oct. 13, 2004

(86) PCT No.: PCT/US2004/033818
§ 371 (c)(1),
(2), (4) Date: Apr. 13, 2006

(87) PCT Pub. No.: WO2005/038039
PCT Pub. Date: Apr. 28, 2005

(65) Prior Publication Data
US 2007/0141575 A1    Jun. 21, 2007

Related U.S. Application Data

(60) Provisional application No. 60/510,762, filed on Oct. 13, 2003.

(51) Int. Cl.
*C12Q 1/68* (2006.01)
*C12P 19/34* (2006.01)
(52) U.S. Cl. .......................... 435/6; 435/91.2
(58) Field of Classification Search ........................ None
See application file for complete search history.

(56) References Cited

U.S. PATENT DOCUMENTS 4,683,202 A    7/1987    Mullis
(Continued)

FOREIGN PATENT DOCUMENTS

EP    91112959.1    8/1991
(Continued)

OTHER PUBLICATIONS

Elnifro et al., Multiplex PCR: Optimization and Application in Diagnostic Virology, Clinical Microbiology Reviews, Oct. 2000, p. 559-570.*

(Continued)

Primary Examiner—Mark Staples
(74) Attorney, Agent, or Firm—Bradley Arant Boult Cummings LLP

(57) ABSTRACT

Disclosed is a novel method for diagnosis or differential diagnosis of disease agents and secondary disease agents. The method disclosed uses a novel amplification strategy termed TemPCR to allow sensitive and specific amplification of target sequences from any disease agents and/or secondary disease agent whose nucleic acid sequence is known. The TemPCR method utilizes at least one set of target enrichment primers specific for the disease agent or secondary disease agent to be detected (present at a low concentration) and at least one pair of shared target amplification primers (present at high concentrations). At least one pair of said target enrichment primers comprises a binding sequence for the target amplification primers. Therefore, the use of the TemPCR method allows multiplex amplification reactions to be carried out without the need for empirical optimization of the multiplex amplification parameters. Methods for nucleic acid isolation and the detection of the target sequences are also disclosed for use with the TemPCR method.

39 Claims, 3 Drawing Sheets

U.S. PATENT DOCUMENTS

| | | | |
|---|---|---|---|
| 5,194,300 A * | 3/1993 | Cheung | 427/213.31 |
| 5,314,809 A * | 5/1994 | Erlich et al. | 435/91.2 |
| 5,340,728 A | 8/1994 | Grosz et al. | |
| 5,422,252 A | 6/1995 | Walker et al. | |
| 5,624,825 A | 4/1997 | Walker et al. | |
| 5,811,235 A * | 9/1998 | Jeffreys | 435/6 |
| 5,882,856 A * | 3/1999 | Shuber | 435/6 |
| 6,168,917 B1 | 1/2001 | Kilpatrick | |
| 6,509,157 B1 | 1/2003 | Martinez | |
| 6,566,067 B2 | 5/2003 | Malo | |
| 6,605,451 B1 | 8/2003 | Marmaro et al. | |
| 6,737,253 B1 | 5/2004 | Tillet | |
| 7,262,030 B2 * | 8/2007 | Chen | 435/91.2 |
| 2003/0096277 A1 * | 5/2003 | Chen | 435/6 |
| 2003/0104459 A1 | 6/2003 | Faham et al. | |
| 2004/0091879 A1 | 5/2004 | Nolan et al. | |
| 2005/0175996 A1 | 8/2005 | Chen | |
| 2006/0035222 A1 * | 2/2006 | Rudi et al. | 435/6 |

FOREIGN PATENT DOCUMENTS

| | | |
|---|---|---|
| EP | 94305400.7 | 7/1994 |
| WO | WO 0194634 | 12/2001 |
| WO | WO 03060159 | 7/2003 |
| WO | WO 03066897 | 8/2003 |

OTHER PUBLICATIONS

Qiagen, Taq PCR Handbook, Mar. 2002, pp. 1-40.*

Archard et al., Characterization of Coxsackie B Virus RNA in Myocardium From Patients With Dilated Cardiomyopathy by Nucleotide Sequencing of Reverse Transcription-Nested Polymerase Chain Reaction Products, Human Pathology vol. 29, No. 6 (Jun. 1998), pp. 578-584.*

* cited by examiner

Analysis

SEQUENCE LISTING

<160> NUMBER OF SEQ ID NOS: 148

<210> SEQ ID NO 1
<211> LENGTH: 23
<212> TYPE: DNA
<213> ORGANISM: Artificial
<220> FEATURE:
<223> OTHER INFORMATION: primer sequence

<400> SEQUENCE: 1
accgtagact catctctatg atg          23

<210> SEQ ID NO 2
<211> LENGTH: 40
<212> TYPE: DNA
<213> ORGANISM: Artificial
<220> FEATURE:
<223> OTHER INFORMATION: primer sequence

<400> SEQUENCE: 2
caggccacgt tttgtcatgc gaagctattc gtcacgttcg          40

<210> SEQ ID NO 3
<211> LENGTH: 24
<212> TYPE: DNA
<213> ORGANISM: Artificial
<220> FEATURE:

<223> OTHER INFORMATION: primer sequence

<400> SEQUENCE: 3
ttgcattaac tctggtgaat tctg                                          24

<210> SEQ ID NO 4
<211> LENGTH: 40
<212> TYPE: DNA
<213> ORGANISM: Artificial
<220> FEATURE:
<223> OTHER INFORMATION: primer sequence

<400> SEQUENCE: 4
ttctttgcgt tatgtctctg ctgtagaaaa tcctagctgg                         40

<210> SEQ ID NO 5
<211> LENGTH: 20
<212> TYPE: DNA
<213> ORGANISM: Artificial
<220> FEATURE:
<223> OTHER INFORMATION: primer sequence

<400> SEQUENCE: 5
tagagggctg tcatgcaact                                               20

<210> SEQ ID NO 6
<211> LENGTH: 24
<212> TYPE: DNA
<213> ORGANISM: Artificial
<220> FEATURE:
<223> OTHER INFORMATION: primer sequence

<400> SEQUENCE: 6
atgcctaaca tgcttaggat aatg                                          24

<210> SEQ ID NO 7
<211> LENGTH: 41
<212> TYPE: DNA
<213> ORGANISM: Artificial
<220> FEATURE:
<223> OTHER INFORMATION: primer sequence

<400> SEQUENCE: 7
caggccacgt tttgtcatgc tttctacagg ttagctaacg a                       41

<210> SEQ ID NO 8
<211> LENGTH: 23
<212> TYPE: DNA
<213> ORGANISM: Artificial
<220> FEATURE:
<223> OTHER INFORMATION: primer sequence

<400> SEQUENCE: 8
tacattggct gtaacagctt gac                                           23

<210> SEQ ID NO 9
<211> LENGTH: 41
<212> TYPE: DNA
<213> ORGANISM: Artificial
<220> FEATURE:
<223> OTHER INFORMATION: primer sequence

<400> SEQUENCE: 9
ttctttgcgt tatgtctctg agcataagca gttgtagcat c                       41

```
<210> SEQ ID NO 10
<211> LENGTH: 20
<212> TYPE: DNA
<213> ORGANISM: Artificial
<220> FEATURE:
<223> OTHER INFORMATION: primer sequence

<400> SEQUENCE: 10
gtgagatggt catgtgtggc                                              20

<210> SEQ ID NO 11
<211> LENGTH: 21
<212> TYPE: DNA
<213> ORGANISM: Artificial
<220> FEATURE:
<223> OTHER INFORMATION: primer sequence

<400> SEQUENCE: 11
acaatgctgc caccgtgcta c                                            21

<210> SEQ ID NO 12
<211> LENGTH: 40
<212> TYPE: DNA
<213> ORGANISM: Artificial
<220> FEATURE:
<223> OTHER INFORMATION: primer sequence

<400> SEQUENCE: 12
caggccacgt tttgtcatgc cctcaaggaa caacattgcc                        40

<210> SEQ ID NO 13
<211> LENGTH: 20
<212> TYPE: DNA
<213> ORGANISM: Artificial
<220> FEATURE:
<223> OTHER INFORMATION: primer sequence

<400> SEQUENCE: 13
tagcgcgagg gcagtttcac                                              20

<210> SEQ ID NO 14
<211> LENGTH: 40
<212> TYPE: DNA
<213> ORGANISM: Artificial
<220> FEATURE:
<223> OTHER INFORMATION: primer sequence

<400> SEQUENCE: 14
ttctttgcgt tatgtctctg ccgctagcca ttcgagcagg                        40

<210> SEQ ID NO 15
<211> LENGTH: 21
<212> TYPE: DNA
<213> ORGANISM: Artificial
<220> FEATURE:
<223> OTHER INFORMATION: primer sequence

<400> SEQUENCE: 15
atcatcacgt agtcgcggta a                                            21

<210> SEQ ID NO 16
<211> LENGTH: 20
<212> TYPE: DNA
<213> ORGANISM: Artificial
<220> FEATURE:
<223> OTHER INFORMATION: primer sequence
```

```
<400> SEQUENCE: 16
attggcatta agcctacaaa                                              20

<210> SEQ ID NO 17
<211> LENGTH: 41
<212> TYPE: DNA
<213> ORGANISM: Artificial
<220> FEATURE:
<223> OTHER INFORMATION: primer sequence

<400> SEQUENCE: 17
caggccacgt tttgtcatgc gggcaaatac aaagatggct c                      41

<210> SEQ ID NO 18
<211> LENGTH: 24
<212> TYPE: DNA
<213> ORGANISM: Artificial
<220> FEATURE:
<223> OTHER INFORMATION: primer sequence

<400> SEQUENCE: 18
gacatagcat ataacatacc tatt                                         24

<210> SEQ ID NO 19
<211> LENGTH: 43
<212> TYPE: DNA
<213> ORGANISM: Artificial
<220> FEATURE:
<223> OTHER INFORMATION: primer sequence

<400> SEQUENCE: 19
ttctttgcgt tatgtctctg ggagtrtcaa taytatctcc tgt                    43

<210> SEQ ID NO 20
<211> LENGTH: 20
<212> TYPE: DNA
<213> ORGANISM: Artificial
<220> FEATURE:
<223> OTHER INFORMATION: primer sequence

<400> SEQUENCE: 20
cactcaacaa agatcaactt                                              20

<210> SEQ ID NO 21
<211> LENGTH: 20
<212> TYPE: DNA
<213> ORGANISM: Artificial
<220> FEATURE:
<223> OTHER INFORMATION: primer sequence

<400> SEQUENCE: 21
attggcatta agcctacaaa                                              20

<210> SEQ ID NO 22
<211> LENGTH: 41
<212> TYPE: DNA
<213> ORGANISM: Artificial
<220> FEATURE:
<223> OTHER INFORMATION: primer sequence

<400> SEQUENCE: 22
caggccacgt tttgtcatgc gggcaaatac aaagatggct c                      41

<210> SEQ ID NO 23
<211> LENGTH: 24
```

```
<212> TYPE: DNA
<213> ORGANISM: Artificial
<220> FEATURE:
<223> OTHER INFORMATION: primer sequence

<400> SEQUENCE: 23
gacatagcat ataacatacc tatt                                              24

<210> SEQ ID NO 24
<211> LENGTH: 43
<212> TYPE: DNA
<213> ORGANISM: Artificial
<220> FEATURE:
<223> OTHER INFORMATION: primer sequence

<400> SEQUENCE: 24
ttctttgcgt tatgtctctg ggagtrtcaa taytatctcc tgt                         43

<210> SEQ ID NO 25
<211> LENGTH: 20
<212> TYPE: DNA
<213> ORGANISM: Artificial
<220> FEATURE:
<223> OTHER INFORMATION: primer sequence

<400> SEQUENCE: 25
cattaaataa ggatcagctg                                                   20

<210> SEQ ID NO 26
<211> LENGTH: 22
<212> TYPE: DNA
<213> ORGANISM: Artificial
<220> FEATURE:
<223> OTHER INFORMATION: primer sequence

<400> SEQUENCE: 26
cacaattgat atgaattatt gg                                                22

<210> SEQ ID NO 27
<211> LENGTH: 44
<212> TYPE: DNA
<213> ORGANISM: Artificial
<220> FEATURE:
<223> OTHER INFORMATION: primer sequence

<400> SEQUENCE: 27
caggccacgt tttgtcatgc tgatgaaata attagagcaa ctag                        44

<210> SEQ ID NO 28
<211> LENGTH: 21
<212> TYPE: DNA
<213> ORGANISM: Artificial
<220> FEATURE:
<223> OTHER INFORMATION: primer sequence

<400> SEQUENCE: 28
ctattwatat catcatcatt t                                                 21

<210> SEQ ID NO 29
<211> LENGTH: 42
<212> TYPE: DNA
<213> ORGANISM: Artificial
<220> FEATURE:
<223> OTHER INFORMATION: primer sequence

<400> SEQUENCE: 29
```
ttctttgcgt tatgtctctg tgctatcatt tctttaagat tg                    42

<210> SEQ ID NO 30
<211> LENGTH: 20
<212> TYPE: DNA
<213> ORGANISM: Artificial
<220> FEATURE:
<223> OTHER INFORMATION: primer sequence

<400> SEQUENCE: 30
cagctatgac tattgcagac                                             20

<210> SEQ ID NO 31
<211> LENGTH: 22
<212> TYPE: DNA
<213> ORGANISM: Artificial
<220> FEATURE:
<223> OTHER INFORMATION: primer sequence

<400> SEQUENCE: 31
cacaattgat atgaattatt gg                                          22

<210> SEQ ID NO 32
<211> LENGTH: 44
<212> TYPE: DNA
<213> ORGANISM: Artificial
<220> FEATURE:
<223> OTHER INFORMATION: primer sequence

<400> SEQUENCE: 32
caggccacgt tttgtcatgc tactgacatc atacatgcaa tttc                  44

<210> SEQ ID NO 33
<211> LENGTH: 21
<212> TYPE: DNA
<213> ORGANISM: Artificial
<220> FEATURE:
<223> OTHER INFORMATION: primer sequence

<400> SEQUENCE: 33
ctattwatat catcatcatt t                                           21

<210> SEQ ID NO 34
<211> LENGTH: 42
<212> TYPE: DNA
<213> ORGANISM: Artificial
<220> FEATURE:
<223> OTHER INFORMATION: primer sequence

<400> SEQUENCE: 34
ttctttgcgt tatgtctctg taactattat ctcttttaaa tt                    42

<210> SEQ ID NO 35
<211> LENGTH: 20
<212> TYPE: DNA
<213> ORGANISM: Artificial
<220> FEATURE:
<223> OTHER INFORMATION: primer sequence

<400> SEQUENCE: 35
ctgcaattac aatagcagat                                             20

<210> SEQ ID NO 36
<211> LENGTH: 20
<212> TYPE: DNA
<213> ORGANISM: Artificial

```
<220> FEATURE:
<223> OTHER INFORMATION: primer sequence

<400> SEQUENCE: 36
accagcataa gaacctcctg                                                   20

<210> SEQ ID NO 37
<211> LENGTH: 41
<212> TYPE: DNA
<213> ORGANISM: Artificial
<220> FEATURE:
<223> OTHER INFORMATION: primer sequence

<400> SEQUENCE: 37
caggccacgt tttgtcatgc tcaagtcacg tactcgccat c                            41

<210> SEQ ID NO 38
<211> LENGTH: 20
<212> TYPE: DNA
<213> ORGANISM: Artificial
<220> FEATURE:
<223> OTHER INFORMATION: primer sequence

<400> SEQUENCE: 38
ttaaactgtt actgttgtgc                                                   20

<210> SEQ ID NO 39
<211> LENGTH: 41
<212> TYPE: DNA
<213> ORGANISM: Artificial
<220> FEATURE:
<223> OTHER INFORMATION: primer sequence

<400> SEQUENCE: 39
ttctttgcgt tatgtctctg tttgcgagat ctcgaggggt c                            41

<210> SEQ ID NO 40
<211> LENGTH: 20
<212> TYPE: DNA
<213> ORGANISM: Artificial
<220> FEATURE:
<223> OTHER INFORMATION: primer sequence

<400> SEQUENCE: 40
gctgaataaa ccgggtatta                                                   20

<210> SEQ ID NO 41
<211> LENGTH: 21
<212> TYPE: DNA
<213> ORGANISM: Artificial
<220> FEATURE:
<223> OTHER INFORMATION: primer sequence

<400> SEQUENCE: 41
gcctgcccta tgaaaacgat g                                                 21

<210> SEQ ID NO 42
<211> LENGTH: 41
<212> TYPE: DNA
<213> ORGANISM: Artificial
<220> FEATURE:
<223> OTHER INFORMATION: primer sequence

<400> SEQUENCE: 42
caggccacgt tttgtcatgc cgtgatccac acgagtcata c                            41
```

<210> SEQ ID NO 43
<211> LENGTH: 21
<212> TYPE: DNA
<213> ORGANISM: Artificial
<220> FEATURE:
<223> OTHER INFORMATION: primer sequence

<400> SEQUENCE: 43
taaagctgct tcgggaacgt g                                              21

<210> SEQ ID NO 44
<211> LENGTH: 41
<212> TYPE: DNA
<213> ORGANISM: Artificial
<220> FEATURE:
<223> OTHER INFORMATION: primer sequence

<400> SEQUENCE: 44
ttctttgcgt tatgtctctg tatcggggtt gtatttcctt c                        41

<210> SEQ ID NO 45
<211> LENGTH: 20
<212> TYPE: DNA
<213> ORGANISM: Artificial
<220> FEATURE:
<223> OTHER INFORMATION: primer sequence

<400> SEQUENCE: 45
atcggaagtc gctctatctt                                                20

<210> SEQ ID NO 46
<211> LENGTH: 20
<212> TYPE: DNA
<213> ORGANISM: Artificial
<220> FEATURE:
<223> OTHER INFORMATION: primer sequence

<400> SEQUENCE: 46
cctccggccc ctgaatgcgg                                                20

<210> SEQ ID NO 47
<211> LENGTH: 41
<212> TYPE: DNA
<213> ORGANISM: Artificial
<220> FEATURE:
<223> OTHER INFORMATION: primer sequence

<400> SEQUENCE: 47
caggccacgt tttgtcatgc cctaactgtg gagcacatgc c                        41

<210> SEQ ID NO 48
<211> LENGTH: 21
<212> TYPE: DNA
<213> ORGANISM: Artificial
<220> FEATURE:
<223> OTHER INFORMATION: primer sequence

<400> SEQUENCE: 48
tgtcaccata agcagccaat g                                              21

<210> SEQ ID NO 49
<211> LENGTH: 40
<212> TYPE: DNA
<213> ORGANISM: Artificial
<220> FEATURE:
<223> OTHER INFORMATION: primer sequence

<400> SEQUENCE: 49
ttctttgcgt tatgtctctg tagtcggttc cgctgcagag         40

<210> SEQ ID NO 50
<211> LENGTH: 20
<212> TYPE: DNA
<213> ORGANISM: Artificial
<220> FEATURE:
<223> OTHER INFORMATION: primer sequence

<400> SEQUENCE: 50
ccagagggta gtgtgtcgta         20

<210> SEQ ID NO 51
<211> LENGTH: 21
<212> TYPE: DNA
<213> ORGANISM: Artificial
<220> FEATURE:
<223> OTHER INFORMATION: primer sequence

<400> SEQUENCE: 51
tgcaattggg gtcctcatcg g         21

<210> SEQ ID NO 52
<211> LENGTH: 41
<212> TYPE: DNA
<213> ORGANISM: Artificial
<220> FEATURE:
<223> OTHER INFORMATION: primer sequence

<400> SEQUENCE: 52
caggccacgt tttgtcatgc ttgaatggaa tgataacaca g         41

<210> SEQ ID NO 53
<211> LENGTH: 21
<212> TYPE: DNA
<213> ORGANISM: Artificial
<220> FEATURE:
<223> OTHER INFORMATION: primer sequence

<400> SEQUENCE: 53
aaacgagaaa gttcttatct c         21

<210> SEQ ID NO 54
<211> LENGTH: 41
<212> TYPE: DNA
<213> ORGANISM: Artificial
<220> FEATURE:
<223> OTHER INFORMATION: primer sequence

<400> SEQUENCE: 54
ttctttgcgt tatgtctctg gttctcgcca ttttccgttt c         41

<210> SEQ ID NO 55
<211> LENGTH: 19
<212> TYPE: DNA
<213> ORGANISM: Artificial
<220> FEATURE:
<223> OTHER INFORMATION: primer sequence

<400> SEQUENCE: 55
tctacagaga ttcgcttgg         19

<210> SEQ ID NO 56

<210> SEQ ID NO 56
<211> LENGTH: 21
<212> TYPE: DNA
<213> ORGANISM: Artificial
<220> FEATURE:
<223> OTHER INFORMATION: primer sequence

<400> SEQUENCE: 56
tgaagggttt gagccatact g                                     21

<210> SEQ ID NO 57
<211> LENGTH: 41
<212> TYPE: DNA
<213> ORGANISM: Artificial
<220> FEATURE:
<223> OTHER INFORMATION: primer sequence

<400> SEQUENCE: 57
caggccacgt tttgtcatgc tacaattgga ccgattaccc t               41

<210> SEQ ID NO 58
<211> LENGTH: 24
<212> TYPE: DNA
<213> ORGANISM: Artificial
<220> FEATURE:
<223> OTHER INFORMATION: primer sequence

<400> SEQUENCE: 58
tgagtgttta cttcctcctt tatc                                  24

<210> SEQ ID NO 59
<211> LENGTH: 42
<212> TYPE: DNA
<213> ORGANISM: Artificial
<220> FEATURE:
<223> OTHER INFORMATION: primer sequence

<400> SEQUENCE: 59
ttctttgcgt tatgtctctg gttgttcatg tcccttaata ct              42

<210> SEQ ID NO 60
<211> LENGTH: 20
<212> TYPE: DNA
<213> ORGANISM: Artificial
<220> FEATURE:
<223> OTHER INFORMATION: primer sequence

<400> SEQUENCE: 60
ccttgatgac atagaagaag                                       20

<210> SEQ ID NO 61
<211> LENGTH: 20
<212> TYPE: DNA
<213> ORGANISM: Artificial
<220> FEATURE:
<223> OTHER INFORMATION: primer sequence

<400> SEQUENCE: 61
aacagaccca aytacattgg                                       20

<210> SEQ ID NO 62
<211> LENGTH: 40
<212> TYPE: DNA
<213> ORGANISM: Artificial
<220> FEATURE:
<223> OTHER INFORMATION: primer sequence

<400> SEQUENCE: 62
caggccacgt tttgtcatgc atgtactaca acagtactgg                                40

<210> SEQ ID NO 63
<211> LENGTH: 23
<212> TYPE: DNA
<213> ORGANISM: Artificial
<220> FEATURE:
<223> OTHER INFORMATION: primer sequence

<400> SEQUENCE: 63
tatgacagtt cwgtgtttct gtc                                                  23

<210> SEQ ID NO 64
<211> LENGTH: 40
<212> TYPE: DNA
<213> ORGANISM: Artificial
<220> FEATURE:
<223> OTHER INFORMATION: primer sequence

<400> SEQUENCE: 64
ttctttgcgt tatgtctctg gcaagtcaac cacggcattc                                40

<210> SEQ ID NO 65
<211> LENGTH: 20
<212> TYPE: DNA
<213> ORGANISM: Artificial
<220> FEATURE:
<223> OTHER INFORMATION: primer sequence

<400> SEQUENCE: 65
gagtgctggc aggtcaagca                                                      20

<210> SEQ ID NO 66
<211> LENGTH: 20
<212> TYPE: DNA
<213> ORGANISM: Artificial
<220> FEATURE:
<223> OTHER INFORMATION: primer sequence

<400> SEQUENCE: 66
gagttttggc tggccaagca                                                      20

<210> SEQ ID NO 67
<211> LENGTH: 20
<212> TYPE: DNA
<213> ORGANISM: Artificial
<220> FEATURE:
<223> OTHER INFORMATION: primer sequence

<400> SEQUENCE: 67
gagttttggc tggccaagca                                                      20

<210> SEQ ID NO 68
<211> LENGTH: 20
<212> TYPE: DNA
<213> ORGANISM: Artificial
<220> FEATURE:
<223> OTHER INFORMATION: primer sequence

<400> SEQUENCE: 68
gggtactggc cggtcaggcc                                                      20

<210> SEQ ID NO 69
<211> LENGTH: 20
<212> TYPE: DNA

```
<213> ORGANISM: Artificial
<220> FEATURE:
<223> OTHER INFORMATION: primer sequence

<400> SEQUENCE: 69
gagttttggc cggccaagca                                          20

<210> SEQ ID NO 70
<211> LENGTH: 20
<212> TYPE: DNA
<213> ORGANISM: Artificial
<220> FEATURE:
<223> OTHER INFORMATION: primer sequence

<400> SEQUENCE: 70
gggtgctggc tggccaagca                                          20

<210> SEQ ID NO 71
<211> LENGTH: 20
<212> TYPE: DNA
<213> ORGANISM: Artificial
<220> FEATURE:
<223> OTHER INFORMATION: primer sequence

<400> SEQUENCE: 71
caggccacgt tttgtcatgc                                          20

<210> SEQ ID NO 72
<211> LENGTH: 20
<212> TYPE: DNA
<213> ORGANISM: Artificial
<220> FEATURE:
<223> OTHER INFORMATION: primer sequence

<400> SEQUENCE: 72
ttctttgcgt tatgtctctg                                          20

<210> SEQ ID NO 73
<211> LENGTH: 23
<212> TYPE: DNA
<213> ORGANISM: Artificial
<220> FEATURE:
<223> OTHER INFORMATION: primer sequence

<400> SEQUENCE: 73
accgtagact catctctatg atg                                      23

<210> SEQ ID NO 74
<211> LENGTH: 40
<212> TYPE: DNA
<213> ORGANISM: Artificial
<220> FEATURE:
<223> OTHER INFORMATION: primer sequence

<400> SEQUENCE: 74
caggccacgt tttgtcatgc gaagctattc gtcacgttcg                    40

<210> SEQ ID NO 75
<211> LENGTH: 24
<212> TYPE: DNA
<213> ORGANISM: Artificial
<220> FEATURE:
<223> OTHER INFORMATION: primer sequence

<400> SEQUENCE: 75
ttgcattaac tctggtgaat tctg                                     24
```

<210> SEQ ID NO 76
<211> LENGTH: 40
<212> TYPE: DNA
<213> ORGANISM: Artificial
<220> FEATURE:
<223> OTHER INFORMATION: primer sequence

<400> SEQUENCE: 76
ttctttgcgt tatgtctctg ctgtagaaaa tcctagctgg            40

<210> SEQ ID NO 77
<211> LENGTH: 20
<212> TYPE: DNA
<213> ORGANISM: Artificial
<220> FEATURE:
<223> OTHER INFORMATION: primer sequence

<400> SEQUENCE: 77
tagagggctg tcatgcaact            20

<210> SEQ ID NO 78
<211> LENGTH: 24
<212> TYPE: DNA
<213> ORGANISM: Artificial
<220> FEATURE:
<223> OTHER INFORMATION: primer sequence

<400> SEQUENCE: 78
atgcctaaca tgcttaggat aatg            24

<210> SEQ ID NO 79
<211> LENGTH: 41
<212> TYPE: DNA
<213> ORGANISM: Artificial
<220> FEATURE:
<223> OTHER INFORMATION: primer sequence

<400> SEQUENCE: 79
caggccacgt tttgtcatgc tttctacagg ttagctaacg a            41

<210> SEQ ID NO 80
<211> LENGTH: 23
<212> TYPE: DNA
<213> ORGANISM: Artificial
<220> FEATURE:
<223> OTHER INFORMATION: primer sequence

<400> SEQUENCE: 80
tacattggct gtaacagctt gac            23

<210> SEQ ID NO 81
<211> LENGTH: 41
<212> TYPE: DNA
<213> ORGANISM: Artificial
<220> FEATURE:
<223> OTHER INFORMATION: primer sequence

<400> SEQUENCE: 81
ttctttgcgt tatgtctctg agcataagca gttgtagcat c            41

<210> SEQ ID NO 82
<211> LENGTH: 20
<212> TYPE: DNA
<213> ORGANISM: Artificial
<220> FEATURE:

```
<223> OTHER INFORMATION: primer sequence

<400> SEQUENCE: 82
gtgagatggt catgtgtggc                                              20

<210> SEQ ID NO 83
<211> LENGTH: 21
<212> TYPE: DNA
<213> ORGANISM: Artificial
<220> FEATURE:
<223> OTHER INFORMATION: primer sequence

<400> SEQUENCE: 83
acaatgctgc caccgtgcta c                                            21

<210> SEQ ID NO 84
<211> LENGTH: 40
<212> TYPE: DNA
<213> ORGANISM: Artificial
<220> FEATURE:
<223> OTHER INFORMATION: primer sequence

<400> SEQUENCE: 84
caggccacgt tttgtcatgc cctcaaggaa caacattgcc                        40

<210> SEQ ID NO 85
<211> LENGTH: 20
<212> TYPE: DNA
<213> ORGANISM: Artificial
<220> FEATURE:
<223> OTHER INFORMATION: primer sequence

<400> SEQUENCE: 85
tagcgcgagg gcagtttcac                                              20

<210> SEQ ID NO 86
<211> LENGTH: 40
<212> TYPE: DNA
<213> ORGANISM: Artificial
<220> FEATURE:
<223> OTHER INFORMATION: primer sequence

<400> SEQUENCE: 86
ttctttgcgt tatgtctctg ccgctagcca ttcgagcagg                        40

<210> SEQ ID NO 87
<211> LENGTH: 20
<212> TYPE: DNA
<213> ORGANISM: Artificial
<220> FEATURE:
<223> OTHER INFORMATION: primer sequence

<400> SEQUENCE: 87
tcatcacgta gtcgcggtaa                                              20

<210> SEQ ID NO 88
<211> LENGTH: 20
<212> TYPE: DNA
<213> ORGANISM: Artificial
<220> FEATURE:
<223> OTHER INFORMATION: primer sequence

<400> SEQUENCE: 88
aagaatttga taagtaccac                                              20
```

<210> SEQ ID NO 89
<211> LENGTH: 40
<212> TYPE: DNA
<213> ORGANISM: Artificial
<220> FEATURE:
<223> OTHER INFORMATION: primer sequence

<400> SEQUENCE: 89
caggccacgt tttgtcatgc actcccttgg ttagagatgg                    40

<210> SEQ ID NO 90
<211> LENGTH: 20
<212> TYPE: DNA
<213> ORGANISM: Artificial
<220> FEATURE:
<223> OTHER INFORMATION: primer sequence

<400> SEQUENCE: 90
tatgtatcac tgccttagcc                                          20

<210> SEQ ID NO 91
<211> LENGTH: 41
<212> TYPE: DNA
<213> ORGANISM: Artificial
<220> FEATURE:
<223> OTHER INFORMATION: primer sequence

<400> SEQUENCE: 91
ttctttgcgt tatgtctctg caatgctact tcatcattgt c                  41

<210> SEQ ID NO 92
<211> LENGTH: 20
<212> TYPE: DNA
<213> ORGANISM: Artificial
<220> FEATURE:
<223> OTHER INFORMATION: primer sequence

<400> SEQUENCE: 92
gcagcaattc attgagtatg                                          20

<210> SEQ ID NO 93
<211> LENGTH: 20
<212> TYPE: DNA
<213> ORGANISM: Artificial
<220> FEATURE:
<223> OTHER INFORMATION: primer sequence

<400> SEQUENCE: 93
aataagaatt tgataagtgc                                          20

<210> SEQ ID NO 94
<211> LENGTH: 40
<212> TYPE: DNA
<213> ORGANISM: Artificial
<220> FEATURE:
<223> OTHER INFORMATION: primer sequence

<400> SEQUENCE: 94
caggccacgt tttgtcatgc acctttcaa tcagaaatgg                     40

<210> SEQ ID NO 95
<211> LENGTH: 20
<212> TYPE: DNA
<213> ORGANISM: Artificial
<220> FEATURE:
<223> OTHER INFORMATION: primer sequence

<400> SEQUENCE: 95
tgctttggct aatgcattgg                                                    20

<210> SEQ ID NO 96
<211> LENGTH: 41
<212> TYPE: DNA
<213> ORGANISM: Artificial
<220> FEATURE:
<223> OTHER INFORMATION: primer sequence

<400> SEQUENCE: 96
ttctttgcgt tatgtctctg caatgctact tcgtcattgt c                             41

<210> SEQ ID NO 97
<211> LENGTH: 20
<212> TYPE: DNA
<213> ORGANISM: Artificial
<220> FEATURE:
<223> OTHER INFORMATION: primer sequence

<400> SEQUENCE: 97
ggtgcaattc actgagcatg                                                    20

<210> SEQ ID NO 98
<211> LENGTH: 20
<212> TYPE: DNA
<213> ORGANISM: Artificial
<220> FEATURE:
<223> OTHER INFORMATION: primer sequence

<400> SEQUENCE: 98
agtatcactc cttgcaatgg                                                    20

<210> SEQ ID NO 99
<211> LENGTH: 40
<212> TYPE: DNA
<213> ORGANISM: Artificial
<220> FEATURE:
<223> OTHER INFORMATION: primer sequence

<400> SEQUENCE: 99
caggccacgt tttgtcatgc atctcactac aaacggtgtc                              40

<210> SEQ ID NO 100
<211> LENGTH: 20
<212> TYPE: DNA
<213> ORGANISM: Artificial
<220> FEATURE:
<223> OTHER INFORMATION: primer sequence

<400> SEQUENCE: 100
gttctttcat actccatgtc                                                    20

<210> SEQ ID NO 101
<211> LENGTH: 40
<212> TYPE: DNA
<213> ORGANISM: Artificial
<220> FEATURE:
<223> OTHER INFORMATION: primer sequence

<400> SEQUENCE: 101
ttctttgcgt tatgtctctg tttgacaatg aacccatctg                              40

<210> SEQ ID NO 102
<211> LENGTH: 20

<212> TYPE: DNA
<213> ORGANISM: Artificial
<220> FEATURE:
<223> OTHER INFORMATION: primer sequence

<400> SEQUENCE: 102
gctgatgtca agtatgtgat                                          20

<210> SEQ ID NO 103
<211> LENGTH: 20
<212> TYPE: DNA
<213> ORGANISM: Artificial
<220> FEATURE:
<223> OTHER INFORMATION: primer sequence

<400> SEQUENCE: 103
tcaatggctt atgccaatcc                                          20

<210> SEQ ID NO 104
<211> LENGTH: 40
<212> TYPE: DNA
<213> ORGANISM: Artificial
<220> FEATURE:
<223> OTHER INFORMATION: primer sequence

<400> SEQUENCE: 104
caggccacgt tttgtcatgc acaacaaatg gaagtaatgc                    40

<210> SEQ ID NO 105
<211> LENGTH: 20
<212> TYPE: DNA
<213> ORGANISM: Artificial
<220> FEATURE:
<223> OTHER INFORMATION: primer sequence

<400> SEQUENCE: 105
caggtcactt ccaaatatcc                                          20

<210> SEQ ID NO 106
<211> LENGTH: 40
<212> TYPE: DNA
<213> ORGANISM: Artificial
<220> FEATURE:
<223> OTHER INFORMATION: primer sequence

<400> SEQUENCE: 106
ttctttgcgt tatgtctctg ctcgtcttaa ccacaaatcc                    40

<210> SEQ ID NO 107
<211> LENGTH: 20
<212> TYPE: DNA
<213> ORGANISM: Artificial
<220> FEATURE:
<223> OTHER INFORMATION: primer sequence

<400> SEQUENCE: 107
ctaaaacggc aaaagtatgg                                          20

<210> SEQ ID NO 108
<211> LENGTH: 21
<212> TYPE: DNA
<213> ORGANISM: Artificial
<220> FEATURE:
<223> OTHER INFORMATION: primer sequence

<400> SEQUENCE: 108

-continued

| tgcaattggg gtcctcatcg g | 21 |

<210> SEQ ID NO 109
<211> LENGTH: 41
<212> TYPE: DNA
<213> ORGANISM: Artificial
<220> FEATURE:
<223> OTHER INFORMATION: primer sequence

<400> SEQUENCE: 109

| caggccacgt tttgtcatgc ttgaatggaa tgataacaca g | 41 |

<210> SEQ ID NO 110
<211> LENGTH: 21
<212> TYPE: DNA
<213> ORGANISM: Artificial
<220> FEATURE:
<223> OTHER INFORMATION: primer sequence

<400> SEQUENCE: 110

| aaacgagaaa gttcttatct c | 21 |

<210> SEQ ID NO 111
<211> LENGTH: 41
<212> TYPE: DNA
<213> ORGANISM: Artificial
<220> FEATURE:
<223> OTHER INFORMATION: primer sequence

<400> SEQUENCE: 111

| ttctttgcgt tatgtctctg gttctcgcca ttttccgttt c | 41 |

<210> SEQ ID NO 112
<211> LENGTH: 19
<212> TYPE: DNA
<213> ORGANISM: Artificial
<220> FEATURE:
<223> OTHER INFORMATION: primer sequence

<400> SEQUENCE: 112

| tctacagaga ttcgcttgg | 19 |

<210> SEQ ID NO 113
<211> LENGTH: 20
<212> TYPE: DNA
<213> ORGANISM: Artificial
<220> FEATURE:
<223> OTHER INFORMATION: primer sequence

<400> SEQUENCE: 113

| agtcttatcc caatttggtc | 20 |

<210> SEQ ID NO 114
<211> LENGTH: 40
<212> TYPE: DNA
<213> ORGANISM: Artificial
<220> FEATURE:
<223> OTHER INFORMATION: primer sequence

<400> SEQUENCE: 114

| caggccacgt tttgtcatgc agagcaccga ttatcaccag | 40 |

<210> SEQ ID NO 115
<211> LENGTH: 20
<212> TYPE: DNA
<213> ORGANISM: Artificial

```
<220> FEATURE:
<223> OTHER INFORMATION: primer sequence

<400> SEQUENCE: 115
aagcactgcc tgctgtacac                                            20

<210> SEQ ID NO 116
<211> LENGTH: 40
<212> TYPE: DNA
<213> ORGANISM: Artificial
<220> FEATURE:
<223> OTHER INFORMATION: primer sequence

<400> SEQUENCE: 116
ttctttgcgt tatgtctctg catgtcagct attatggagc                      40

<210> SEQ ID NO 117
<211> LENGTH: 20
<212> TYPE: DNA
<213> ORGANISM: Artificial
<220> FEATURE:
<223> OTHER INFORMATION: primer sequence

<400> SEQUENCE: 117
ttccacaaaa cagtaatagc                                            20

<210> SEQ ID NO 118
<211> LENGTH: 20
<212> TYPE: DNA
<213> ORGANISM: Artificial
<220> FEATURE:
<223> OTHER INFORMATION: primer sequence

<400> SEQUENCE: 118 atcacccttta accccttttgg                                           20

<210> SEQ ID NO 119
<211> LENGTH: 39
<212> TYPE: DNA
<213> ORGANISM: Artificial
<220> FEATURE:
<223> OTHER INFORMATION: primer sequence

<400> SEQUENCE: 119
caggccacgt tttgtcatgc cggctttggt ttgagtggg                       39

<210> SEQ ID NO 120
<211> LENGTH: 20
<212> TYPE: DNA
<213> ORGANISM: Artificial
<220> FEATURE:
<223> OTHER INFORMATION: primer sequence

<400> SEQUENCE: 120
tgcaactgct catagtacac                                            20

<210> SEQ ID NO 121
<211> LENGTH: 40
<212> TYPE: DNA
<213> ORGANISM: Artificial
<220> FEATURE:
<223> OTHER INFORMATION: primer sequence

<400> SEQUENCE: 121
ttctttgcgt tatgtctctg cgcggcacga gtaaaacggc                      40
```

<210> SEQ ID NO 122
<211> LENGTH: 20
<212> TYPE: DNA
<213> ORGANISM: Artificial
<220> FEATURE:
<223> OTHER INFORMATION: primer sequence

<400> SEQUENCE: 122
tgcaccccaa cagtgaaacg                                          20

<210> SEQ ID NO 123
<211> LENGTH: 21
<212> TYPE: DNA
<213> ORGANISM: Artificial
<220> FEATURE:
<223> OTHER INFORMATION: primer sequence

<400> SEQUENCE: 123
gaaatttata gagccgactc g                                        21

<210> SEQ ID NO 124
<211> LENGTH: 40
<212> TYPE: DNA
<213> ORGANISM: Artificial
<220> FEATURE:
<223> OTHER INFORMATION: primer sequence

<400> SEQUENCE: 124
caggccacgt tttgtcatgc gctgatatca ttgtacatgg                    40

<210> SEQ ID NO 125
<211> LENGTH: 21
<212> TYPE: DNA
<213> ORGANISM: Artificial
<220> FEATURE:
<223> OTHER INFORMATION: primer sequence

<400> SEQUENCE: 125
gttgaccata taatacgtct c                                        21

<210> SEQ ID NO 126
<211> LENGTH: 38
<212> TYPE: DNA
<213> ORGANISM: Artificial
<220> FEATURE:
<223> OTHER INFORMATION: primer sequence

<400> SEQUENCE: 126
ttctttgcgt tatgtctctg gctttccagg gcattctc                      38

<210> SEQ ID NO 127
<211> LENGTH: 20
<212> TYPE: DNA
<213> ORGANISM: Artificial
<220> FEATURE:
<223> OTHER INFORMATION: primer sequence

<400> SEQUENCE: 127
accgacaaaa cgtagtaaca                                          20

<210> SEQ ID NO 128
<211> LENGTH: 21
<212> TYPE: DNA
<213> ORGANISM: Artificial
<220> FEATURE:
<223> OTHER INFORMATION: primer sequence

<400> SEQUENCE: 128
caaggtgtga agagcctatt g					21

<210> SEQ ID NO 129
<211> LENGTH: 21
<212> TYPE: DNA
<213> ORGANISM: Artificial
<220> FEATURE:
<223> OTHER INFORMATION: primer sequence

<400> SEQUENCE: 129
catggtgcga agagtctatt g					21

<210> SEQ ID NO 130
<211> LENGTH: 21
<212> TYPE: DNA
<213> ORGANISM: Artificial
<220> FEATURE:
<223> OTHER INFORMATION: primer sequence

<400> SEQUENCE: 130
gtgaagagcc gccgtgtgct c					21

<210> SEQ ID NO 131
<211> LENGTH: 40
<212> TYPE: DNA
<213> ORGANISM: Artificial
<220> FEATURE:
<223> OTHER INFORMATION: primer sequence

<400> SEQUENCE: 131
ttctttgcgt tatgtctctg agtcctccgg cccctgaatg					40

<210> SEQ ID NO 132
<211> LENGTH: 41
<212> TYPE: DNA
<213> ORGANISM: Artificial
<220> FEATURE:
<223> OTHER INFORMATION: primer sequence

<400> SEQUENCE: 132
caggccacgt tttgtcatgc aaacacggac acccaaagta g					41

<210> SEQ ID NO 133
<211> LENGTH: 19
<212> TYPE: DNA
<213> ORGANISM: Artificial
<220> FEATURE:
<223> OTHER INFORMATION: primer sequence

<400> SEQUENCE: 133
attgtcacca taagcagcc					19

<210> SEQ ID NO 134
<211> LENGTH: 20
<212> TYPE: DNA
<213> ORGANISM: Artificial
<220> FEATURE:
<223> OTHER INFORMATION: primer sequence

<400> SEQUENCE: 134
tatatattgt caccataagc					20

<210> SEQ ID NO 135

```
<211> LENGTH: 20
<212> TYPE: DNA
<213> ORGANISM: Artificial
<220> FEATURE:
<223> OTHER INFORMATION: primer sequence

<400> SEQUENCE: 135
gttaggatta gccgcattca                                                    20

<210> SEQ ID NO 136
<211> LENGTH: 20
<212> TYPE: DNA
<213> ORGANISM: Artificial
<220> FEATURE:
<223> OTHER INFORMATION: primer sequence

<400> SEQUENCE: 136
gttggtccca tcccgcaatt                                                    20

<210> SEQ ID NO 137
<211> LENGTH: 20
<212> TYPE: DNA
<213> ORGANISM: Artificial
<220> FEATURE:
<223> OTHER INFORMATION: primer sequence

<400> SEQUENCE: 137
agcaacttca tgtctatggg                                                    20

<210> SEQ ID NO 138
<211> LENGTH: 39
<212> TYPE: DNA
<213> ORGANISM: Artificial
<220> FEATURE:
<223> OTHER INFORMATION: primer sequence

<400> SEQUENCE: 138
caggccacgt tttgtcatgc cccatggatg agcccaccc                               39

<210> SEQ ID NO 139
<211> LENGTH: 40
<212> TYPE: DNA
<213> ORGANISM: Artificial
<220> FEATURE:
<223> OTHER INFORMATION: primer sequence

<400> SEQUENCE: 139
ttctttgcgt tatgtctctg gctggtgcac tctgaccacg                              40

<210> SEQ ID NO 140
<211> LENGTH: 40
<212> TYPE: DNA
<213> ORGANISM: Artificial
<220> FEATURE:
<223> OTHER INFORMATION: primer sequence

<400> SEQUENCE: 140
ttctttgcgt tatgtctctg gctggtgcac tcggacgacg                              40

<210> SEQ ID NO 141
<211> LENGTH: 40
<212> TYPE: DNA
<213> ORGANISM: Artificial
<220> FEATURE:
<223> OTHER INFORMATION: primer sequence

<400> SEQUENCE: 141
```
ttctttgcgt tatgtctctg gctgatgcac tctgaccacg                     40

<210> SEQ ID NO 142
<211> LENGTH: 20
<212> TYPE: DNA
<213> ORGANISM: Artificial
<220> FEATURE:
<223> OTHER INFORMATION: primer sequence

<400> SEQUENCE: 142
gtgcgcaggt agacggcctc                                           20

<210> SEQ ID NO 143
<211> LENGTH: 20
<212> TYPE: DNA
<213> ORGANISM: Artificial
<220> FEATURE:
<223> OTHER INFORMATION: primer sequence

<400> SEQUENCE: 143
gtacgcaggt agactgtctc                                           20

<210> SEQ ID NO 144
<211> LENGTH: 20
<212> TYPE: DNA
<213> ORGANISM: Artificial
<220> FEATURE:
<223> OTHER INFORMATION: primer sequence

<400> SEQUENCE: 144
gctttatctt cttttcgaag                                           20

<210> SEQ ID NO 145
<211> LENGTH: 20
<212> TYPE: DNA
<213> ORGANISM: Artificial
<220> FEATURE:
<223> OTHER INFORMATION: primer sequence

<400> SEQUENCE: 145
tctctatgtt gtcttcgaag                                           20

<210> SEQ ID NO 146
<211> LENGTH: 20
<212> TYPE: DNA
<213> ORGANISM: Artificial
<220> FEATURE:
<223> OTHER INFORMATION: primer sequence

<400> SEQUENCE: 146
gctttatctt ctcttcgaag                                           20

<210> SEQ ID NO 147
<211> LENGTH: 20
<212> TYPE: DNA
<213> ORGANISM: Artificial
<220> FEATURE:
<223> OTHER INFORMATION: primer sequence

<400> SEQUENCE: 147
caggccacgt tttgtcatgc                                           20

<210> SEQ ID NO 148
<211> LENGTH: 20
<212> TYPE: DNA

```
<213> ORGANISM: Artificial
<220> FEATURE:
<223> OTHER INFORMATION: primer sequence

<400> SEQUENCE: 148
ttctttgcgt tatgtctctg                                            20
```

METHOD AND KIT FOR PRIMER BASED MULTIPLEX AMPLIFICATION OF NUCLEIC ACIDS EMPLOYING PRIMER BINDING TAGS

This application is a national stage application of international application no. PCT/US2004/33818, filed Oct. 13, 2004, which claims priority to and the benefit of U.S. provisional patent application No. 60/510,762, filed Oct. 13, 2003.

BACKGROUND

One important issue for the effective containment and control of any agent is a timely and accurate diagnosis of patients infected with that agent. One aspect of such a diagnosis includes differential diagnosis. By differential diagnosis it is meant the determination and identification of those patients having a disease state or condition caused by a disease agent of interest, and those patients having a disease state condition caused by one or more secondary agents that result in a similar clinical manifestation. This differential diagnosis is critical since the symptoms/clinical manifestations observed in conditions caused by the disease agent of interest may also be observed in conditions caused by the secondary agents. Therefore, the possibility of misdiagnosis is a significant issue. Such misdiagnosis can result in both false positives, and false negatives. Each of these types of misdiagnosis has a detrimental impact of the containment and control of the disease agent. For example, a false negative will allow an infected individual to continue to spread the disease agent to the general population. A false positive will result in an increased burden on the healthcare system and on the individuals required to undergo needless treatment.

False positives and false negatives can be of special concern in cases of bioterrorism, where accurate and rapid identification of the causative agent is required for containment, control and an effective public health response. The growing concern regarding the use of bioterrorism has prompted Federal health agencies to accelerate measures to protect the public from such attacks. In February, 2002, the National Institute of Allergy and Infectious Diseases (NIAID) released its Biodefense Research Agenda for CDC category A, B and C agents. One of the goals of this research agenda was the development of diagnostic test applicable to agents that may be used in bioterrorism. The Agenda stated "A successful response to a bioterrorist threat requires diagnostics that can identify the pathogen involved. However, the initial clinical signs and symptoms of many agents considered biothreats are nonspecific and resemble those of common infections. The ability to rapidly identify the introduction of a bioterrorism organism or toxin will require diagnostic tools that are highly sensitive, specific inexpensive, easy to use, and located in primary care settings."

As an example of the problems and issues discussed above, consider the recent outbreak of the severe acute respiratory syndrome (SARS). The clinical symptoms of SARS, especially in the early stages, included fever, chills and moderate to severe coughing. Obviously, these symptoms are observed in a number of conditions caused by other agents. Other agents capable of causing conditions with SARS-like symptoms include, but are not limited to, respiratory syncytial virus, parainfluenzaviruses type 1 and type 3, influenza A and B viruses, enterovirus, adenovirus, *Mycoplasma pneumoniae*, and *Chlamydia pneumoniae*.

There are three classes of diagnostic tests commonly used in the detection of disease agents: i) ELISA tests; ii) cell culture methods; and iii) molecular tests. Each of these tests has their own advantages and disadvantages. The ELISA (Enzyme Linked Immunoabsorbant Assay) is an antibody test. It detects antibodies to the disease agent in the serum of patients reliably by day 21 after the onset of clinical symptoms. ELISA is specific, but the detection comes too late for detection to be useful in disease management. It can not provide the much needed early information required for the containment and control of the disease agent.

Cell culture methods detect the presence of live agent. A sample is taken from an individual suspected of being infected with the disease agent and the disease agent is propagated in cultured cells or cultured according to defined conditions on selective culture media. Either process is a time-consuming, demanding and dangerous task, but it is the only means to show the existence of the live agent. As with the ELISA, the test is relatively specific, but the detection comes too late for detection to be useful in disease management.

The molecular tests generally use any one of a number of variations on the polymerase chain reaction (PCR). PCR can detect genetic material of an agent in various specimens (blood, stool, respiratory secretions or body tissue) from the individual suspected of being infected by the disease agent. Existing PCR tests are very specific, but lack sensitivity. This is because the agent may not yet be present in the patient specimens or the amplification and detection schemes fail to identify the genetic material. Therefore, a negative test can't rule out the presence of the disease agent in an individual.

Multiplex PCR allows the amplification of target sequences from multiple organisms in one reaction using multiple sets of locus specific primers. Therefore, multiplex PCR is suited to differential diagnosis. However, multiplex PCR methods have limitations. There are two major problems associated with the multiplex PCR method. One is that each target sequence (or locus) to be amplified has its own amplification efficiency. The locus specific amplification efficiency is determined by multiple factors including the composition of the primer targets, binding affinity of the primers to their targets, priming efficiency of the primers and availability of reaction components. Combining multiple target loci in one reaction may introduce incompatibility between various primer sets which results in preferential amplification or inhibition of some amplification reactions. The second issue is the identification of the optimal primer to locus ratio. If the primer concentrations are set too high, primer dimmers and background amplification will occur. If, however, the primer concentrations are too low, the desired exponential amplification of the target sequence will not occur.

In order to optimize multiplex PCR, the concentrations of primers, buffer, dNTPs, enzyme, and $MgCl_2$ need to be determined empirically for each set of primer combinations. It is a time consuming process which needs to be conducted for each lot of the produced assay. A successful multiplex PCR is not guaranteed even after exhaustive optimization experiments.

The present disclosure provides a quick, accurate molecular diagnostic method for the diagnosis of a disease agent and/or the differential diagnosis of a disease agents in the presence of one or more secondary disease agents. Briefly nucleic acid samples are obtained from samples suspected of containing the disease agent and/or secondary disease agents; the nucleic acid may be DNA or RNA (either positive strand or negative strand) or a combination thereof. A multiplex amplification reaction is used to amplify pre-determined target sequences from the nucleic acid through one amplification reaction in one vial. The amplification products containing the target sequences are detected and differentiated using a multiplex detection strategy. The detection of the target sequence from a disease agent or secondary disease agent indicates its presence in the sample. Using the method disclosed herein, a diagnosis or differential diagnosis of a disease agent can be made in as little as 3 hours. The high throughput ability allows the analysis of hundreds of samples per day without the need for complex and time consuming optimization procedures for each primer combination. Such methods are lacking in the art.

DETAILED DESCRIPTION

Figure 1A:
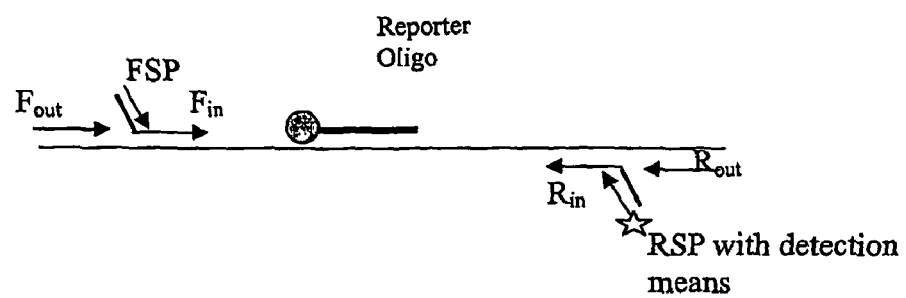
FIGS. 1A and 1B are illustrations of two embodiment of the Tem-PCR amplification process.

The method described herein, termed the Multiplex Analysis System (MAS) provides a rapid and convenient format for diagnosis of disease agents and/or differential diagnosis of disease agents and secondary disease agents. As used in this specification, an "agent" means any organism, regardless of form, that incorporates a nucleic acid and that causes or contributes to an infection, a symptom, or a condition, including, but not limited to a bacteria (list classes), a virus (the virus may have a DNA genome, a negative strand RNA genome or a positive strand RNA genome) or a parasite. The infection, symptom, or condition caused by or related to the disease agent sought to be diagnosed is referred to in this specification as the "disease state". As used in this specification, a "disease agent" means any agent that causes or contributes to disease state sought to be diagnosed. In one embodiment, the disease agent and/or the disease state sought to be diagnosed will be determined in advance by a healthcare provider or other person. In one embodiment the disease agent may be involved in bio-weapons programs, such as the organism described as potential biothreats which are described in the NIAID Biodefense Research Agenda. As discussed herein, the MAS can be used in differential diagnosis. When discussing differential diagnosis, reference will be made to the disease agent and one or more secondary disease agents. As used in this specification, the "secondary disease agent(s)" means any agent that presents a similar clinical presentation to the disease state caused or contributed to be the disease agent. As a result, a differential diagnosis using the MAS will be able to accurately determine the presence of the disease agent if the disease agent is present, as well as the presence of any secondary disease agents that may be present.

As used interchangeably in this disclosure, the terms "nucleic acid molecule(s)", "oligonucleotide(s)", and "polynucleotide(s)" include RNA or DNA (either single or double stranded, coding, complementary or antisense), or RNA/DNA hybrid sequences of more than one nucleotide in either single chain or duplex form (although each of the above species may be particularly specified). The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modification such as (a) an alternative linking group, (b) an analogous form of purine, (c) an analogous form of pyrimidine, or (d) an analogous sugar. The polynucleotide sequences of the invention may be prepared by any known method, including synthetic, recombinant, ex vivo generation, or a combination thereof, as well as utilizing any purification methods known in the art.

The MAS described herein is capable of detecting disease agents that cause or contribute to a variety of disease states. The MAS can be used in differential diagnosis to determine if a specific disease agent is present and to determine if secondary disease agents are present. However, it is not required that the MAS be used in a differential diagnosis application. The MAS can also be used to diagnose the presence or absence of genetic mutations related to disease states, the presence or absence of single nucleotide polymorphisms (SNPs), to determine gene expression profiling, and to determine gene dosage mutations. Applications of these alternative uses of the MAS are described in co-pending U.S. application Ser. No. 10/284,656. Other uses of the MAS will be appreciated by those skilled in the art.

The MAS described may comprise three steps: i) nucleic acid isolation; ii) multiplex amplification to amplify the nucleic acid sequences from the disease agent or secondary disease agent containing the target sequence(s); and iii) multiplexed detection of the target sequences amplified in step (ii). In the embodiment of the MAS described the simultaneous isolation of both RNA (both positive and negative strand) and DNA is provided. Simultaneous isolation of both RNA and DNA is advantageous since the disease agent and the secondary agents may have different nucleic acid genomes. Without dual amplification of DNA and RNA, multiple samples would be required to be tested. In an alternate embodiment, where the disease agent and the secondary disease agents each have an identical type of nucleic acid genome, the nucleic acid isolation step may isolate only one type of nucleic acid. The MAS is highly adaptable, allowing new agents and mutants of known and new agents to be included when they become known through appropriate design of the primer sequences used in the multiplex amplification step. As will be discussed in more detail below, in one embodiment, the multiplex amplification strategy used in the MAS utilizes unique and heretofore unappreciated methods to reduce incompatibility between various primer pairs and to increase sensitivity and specificity of the multiplex amplification reaction over those of currently available methods. The entire MAS procedure can be accomplished in as little as three hours.

The MAS is described generally so that its application can be understood. The MAS method can be used to determine the presence of a disease agent from a sample obtained from an individual suspecting of harboring said disease agent, and to therefore, identify and diagnose those individuals who have a disease state caused by or contributed to by the disease agent. The MAS may be used in differential diagnosis involving the disease agent and one or more secondary disease agents. Although the MAS can be used to determine the presence of any disease agent, an example is provided illustrating the differential diagnosis where SARS is the disease agent, and where respiratory syncytial virus A and B, HPIV 1 and 3, influenza A and B, enterovirus, adenovirus 4 and 21, *C. pneumoniae* and *M. pneumoniae* are the secondary disease agents.

However, the MAS can be used to determine the presence of any disease agent and secondary disease agent through appropriate design of the multiplex amplification.

The various components of the MAS are described in greater detail below. It should be appreciated that while certain embodiments are discussed in regard to these components, other methods known in the art for accomplishing the same ends should be considered within the scope of the present disclosure. In addition, various embodiments of the MAS may use different methods of carrying out the steps described below, depending on the purpose of the MAS, the nature of the disease state, and the nature of the disease agent and one or more secondary disease agents.

Nucleic Acid Isolation

In one embodiment of the MAS, a nucleic acid isolation step is used that isolates both RNA and DNA in one reaction. In an alternate embodiment, RNA and DNA may be isolated independently and then combined for use in the MAS. In yet another alternate embodiment, when only one type of nucleic acid is required to be isolated (such as when all the disease agents and secondary disease agents of interest have the same type of nucleic acid genome), nucleic acid isolation methods that isolate only RNA or DNA may be used. A variety of techniques and protocols are known in the art for simultaneous RNA and DNA isolation and the separate isolation of each and such techniques and protocols may be used. The nucleic acid isolation described may be used to isolate nucleic acid from a variety of patient samples or sources. The types of patient samples/sources include, but are not limited to, nasal/pharyngeal swabs, saliva, sputum, serum, whole blood and stool.

The nucleic acid isolation method may satisfy one or more of the following requirements. First, the nucleic acid isolation method may inactivate any disease agent and any secondary disease agents that may be present in the patient samples. As a result, the risk to laboratory and healthcare personnel is reduced. Furthermore, the remaining steps of the MAS can be completed without the requirement for stringent bio-containment procedures if desired. In addition, the method may allow for the removal or PCR and RT-PCR inhibitors and other unwanted compounds from the isolated nucleic acid.

In one embodiment, a dual RNA/DNA isolation method is used employing a trizol based reagent for initial isolation of RNA and DNA from patient samples. Upon contact with patient samples, the phenol and high salt reagents in the trizol effectively inactivate any disease agent or secondary disease agent that may be present in the patient sample. In order to allow for the dual isolation of RNA and DNA in the same phase with a single step, the pH of the trizol solution may be adjusted towards neutral (instead of acidic). After the RNA and DNA are isolated from the patient samples, a silica based column may be used to further isolate the RNA and DNA. The use of silica based columns allows for wash steps to be performed quickly and efficiently while minimizing the possibility of contamination. The wash steps may be used to remove PCR and RT-PCR inhibitors. The column method for nucleic acid purification is advantageous as it can be used with different types of patient samples and the spin and wash steps effectively remove PCR or RT-PCR inhibitors.

In one embodiment, the nucleic isolation is carried out using the dual RNA/DNA isolation kit provided by Omega Bio-Tek according to manufacturer's instructions. Briefly, 250 µl of subject sample is added to 1 ml of nucleic acid isolation reagent (trizol reagent) followed by 250 µl chloroform. The mixture is thoroughly mixed, such as by vortexing. Samples are centrifuged at 12,000×g for 10 minutes to separate the aqueous and organic phases. The upper aqueous phase is carefully transferred into a new 1.5 ml centrifuge tube. An equal volume of 70% ethanol is added and the samples mixed, such as by vortexing. The sample are applied onto a HiBind spin column set in a collection tube and centrifuged at 10,000×g for 15 seconds. The flow through is discarded. 500 µl of Wash Buffer I is added to the column and the column centrifuged for 15 seconds. The column is washed with 500 µl of Wash Buffer II, twice, for 15 seconds each. The RNA/DNA was eluted by adding 50 µl of RNase-free water and centrifuging at maximum speed for 1 minute. The nucleic acid samples may then be used for the amplification steps as described below.

In addition to the trizol method described above, other methods may be used to isolate RNA and/or DNA. In an alternate embodiment, LNA-conjugated magnetic beads are used. LNA (Locked Nucleic Acids) are a class of nucleic acids containing altered nucleosides whose major distinguishing characteristic is the presence of a methylene bridge between the 2'-O and 4'C atoms of the ribose ring. LNA nucleosides containing the five common nucleobases that appear in DNA and RNA (A,T,U,C,G) can base-pair with their complementary nucleosides according to Watson-Crick rules. The molecular differences between normal nucleosides and LNAs give rise to differences in the stability of nucleic acid duplexes formed between LNA containing nucleic acids and non-LNA containing nucleic acids. Typically, each LNA nucleotide incorporated increases the $T_m$ of a LNA/DNA nucleotide complex by 2-6° C. as compared to a corresponding DNA/DNA complex. LNA-containing oligonucleotides capable of binding to the nucleic acid of disease agent and secondary disease agents (either through specific or non-specific interactions) could be linked to magnetic beads in order to isolate said nucleic acid. The LNA-containing oligonucleotides will bind to nucleic acid of the disease agent or secondary disease agent; separation may then be achieved by a simple magnetic separation and washing step. The process also allows the removal of PCR inhibitors. The LNA-containing oligonucleotide/magnetic bead conjugates could be mixed directly with PCR or RT-PCR reagents for use in the multiplex amplification step. Using the LNA-containing oligonucleotide magnetic beads, patient samples with high volumes can be efficiently processed. The LNA method may be used conjunction with the trizol dual extraction method described above or any other method known in the art or described in this specification for isolating DNA and/or RNA.

Multiplex Amplification

A variety of multiplex amplification strategies may be used with the MAS. Many such amplification strategies are known in the art The multiplex amplification strategy may use PCR, RT-PCR or a combination thereof depending on the type of nucleic acid contained in the disease agent and secondary disease agent. For example, if an RNA genome is present, RT-PCR may be utilized. The methodology of PCR and RT-PCR are well known in the art In one embodiment, the multiplex amplification strategy employed in the MAS is unique. This unique multiplex amplification strategy is termed target enriched multiplex PCR (Tem-PCR) and allows the efficient amplification of one or more target sequences from a disease agent and/or secondary disease agents without extensive empirical testing of primer combinations and amplification conditions as is required with other multiplex amplification methods known in the art As used in this specification, a "target sequence" is a nucleotide sequence from a disease agent or a secondary disease agent that is to be amplified and ultimately detected; the target sequence is contained in a larger nucleic acid sequence amplified by the primer sets described herein. Each target sequence for amplification is selected so that on detection (as discussed below) it allows the identification of a disease agent or secondary disease agent, if either is present in the sample. The detection of the amplified target sequence (either directly or indirectly—see discussion below) will indicate the presence and identity of the disease agent or the secondary disease agent and thereby diagnose the relevant disease state. In one embodiment, a single target sequence is selected for amplification from each disease agent and each secondary disease agent to be tested. In an alternate embodiment, more than one target sequence is selected for amplification from each disease agent and each secondary disease agent. In yet an additional embodiment, more than one target sequence is selected for amplification from the disease agent and a single target sequence is selected for amplification from each secondary disease agent.

Figure 1B:
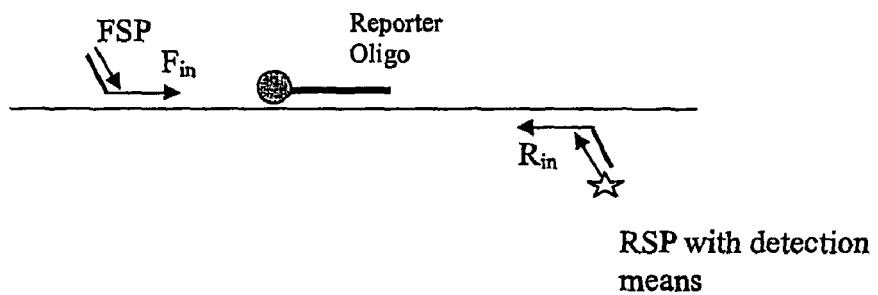

The principle of Tem-PCR is illustrated in FIGS. 1A and 1B. FIG. 1A illustrates the use of 3 primer oligonucleotide pairs for the amplification of the target sequence. The primer oligonucleotides are indicated as $F_{out}$ (outside forward primer) $F_{in}$ (inside forward primer), $R_{out}$ (outside reverse primer), $R_{in}$ (inside reverse primer), FSP (forward super primer) and RSP (reverse super primer). The 3 primer pairs illustrated in FIG. 1 comprise 2 pairs of target enrichment primers ($F_{out}$ and $R_{out}$; and $F_{in}$ and $R_{in}$) and 1 pair of target amplification primers (FSP and RSP). As discussed below, additional target enrichment primers and target amplification primers may be incorporated as desired. The target enrichment primers, in this embodiment, $F_{out}$ and $R_{out}$ and $F_{in}$ and $R_{in}$, are designed to hybridize specifically to the nucleic acid containing the target sequence and to bracket the target sequence as illustrated in FIG. 1A. Therefore, the first set of target enrichment primers, $F_{out}$ and $R_{out}$, binds the nucleic acid containing the target sequence and brackets the target sequence (one of $F_{out}$ and $R_{out}$ is on the 5', or left, side of the target sequence and the other is on the 3', or right, side of the target sequence). The second set of target enrichment primers, $F_{in}$, and $R_{in}$, binds the nucleic acid containing the target sequence and brackets the target sequence as described for the first set of target enrichment primers. The second set of target enrichment primers binds to the inside of the first set of target enrichment primers as shown in FIG. 1A. This location is defined as proximate to the target sequence; in other words, the second set of target enrichment primers binds the nucleic acid containing the target sequence such that the second set of target enrichment primers are located closer to the target sequence as compared to the first set of target enrichment primers.

Each of the primers in at least one of the first or second primer enrichment pairs further comprises a super primer binding tag on its 5' end. The super primer binding tag is an oligonucleotide sequence that is identical to the sequence of the target amplification primers (RSP and FSP). During amplification during the TemPCR process, the primer pair containing the super primer binding tag is copied into its complement to create a binding site for the at least one pair of target amplification primers (FSP and RSP) to allow exponential amplification of the target sequence. In the embodiment shown in FIG. 1A, the second target enrichment primer pair comprises the super primer binding tag, with $F_i$ containing a super primer binding tag identical to the sequence of the FSP and $R_i$ containing a super primer binding tag identical to the sequence of the RSP. The outside primers may comprise the super primer oligonucleotide tag is desired, with the principles of operation being the same as described above.

The specificity of the hybridization between the target enrichment primers and their nucleic acid sequences can be adjusted by increasing or decreasing the length of the primer sequence responsible for hybridization as is known in the art. In general, a shorter primer sequence will give increased specificity while longer primer sequence will provide greater hybridization efficiency. Furthermore, increasing or decreasing the lengths of the primer sequence responsible for hybridization may also determine which primers are active during the various stages of the TemPCR amplifications process (see discussion below). In one embodiment, the length of the target enrichment primers is from 10 to 50 nucleotides. In an alternate embodiment, the length of the target enrichment primers is from 10 to 40 nucleotides. In yet another alternate embodiment, the length of the target enrichment primers is from 10 to 20 nucleotides. The primers in each set of the target enrichment primers may be different lengths if desired. For example, in one embodiment, the target enrichment primers $F_{out}$ and $R_{out}$ are 15-25 nucleotides in length and the target enrichment primers $F_{in}$ and $R_{in}$ are 35 to 45 nucleotides in length (with such length not including the super primer binding tag).

The first set of target amplification primers, FSP and RSP in FIGS. 1A and 1B, are common primer sequences and are used for the universal amplification of nucleic acid amplified during the target enrichment step (which contains the target nucleic acid). In one embodiment, the length of the target amplification primers is from 10 to 50 nucleotides. In an alternate embodiment, the length of the target amplification primers is from 10 to 40 nucleotides. In yet another alternate embodiment, the length of the target amplification primers is from 10 to 20 nucleotides.

The target enrichment primers are used at low concentrations for enrichment (i.e. limited amplification) of the target sequence, while the target amplification primers are used at high concentration for exponential amplification of the target sequences. Since any convenient target sequence can be chose for amplification and detection, the sequence of the nested primers are dictated only by the nature of the nucleic acid sequence flanking the target sequence. Therefore, the target enrichment primers can be designed with minimal constraint on their composition. The use of at least one set of nested primers that does not contain the oligonucleotide tag (such as $F_{out}$ and $R_{out}$ in FIG. 1A) may increases the efficiency of the initial reverse transcription reaction. Multiple sets of target enrichment primers may enhance the sensitivity and specificity of the assay by allowing more opportunity and combinations for the nested primers to work together to provide target sequence enrichment. In addition, since the target enrichment primers are present at low concentrations, are not labeled, and are not responsible for the exponential amplification of the target sequences, the design of the target enrichment primers does not raise significant issues regarding compatibility regarding the various combinations of target enrichment primers. As discussed below, the exponential amplification is carried out by the super primers. This aspect of Tem-PCR allows the simple and rapid modification of the assay to detect additional disease agents and secondary disease agents.

Although the embodiments illustrated in FIGS. 1A and 1B show the use of one or two sets of target enrichment primers to amplify a given nucleic acid containing the target sequence, more than 2 sets of target enrichment primers may be used if desired. In one embodiment, 3 to 6 sets of target enrichment primers are used in the Tem-PCR reaction. In an additional embodiment, 3 to 5 sets of target enrichment primers are used. In an alternate embodiment, 3 to 4 sets of target enrichment primers are used.

More than 1 set of target amplification primers may also be used. When more than 1 set of target amplification primers are used, the sequences of the multiple sets of target amplification primers are selected so that they are compatible with one another in the exponential amplification step. In other words, the multiple sets of super primers would share similar $T_m$s when biding to the super primer binding sites on the amplified target nucleic acid and have similar amplification efficiencies. Multiple target amplification primers may be used when one or more of the disease agent or secondary disease agents are present at different titers/concentrations. If there is a significant difference in titer, then with only 1 set of target amplification primers, preferential amplification of the high titer agent may occur. This could result in a false negative diagnosis for the agent present at the lower titer. Such biased amplification may be avoided by using multiple sets of target amplification primers. In one embodiment, 2-8 sets of target amplification primers are used. In an alternate embodiment, 2-6 sets of target amplification primers are used. In yet another alternate embodiment, 2-4 sets of target amplification primers are used.

The target amplification primers are used at high concentrations. The sequence of the target amplification primers are the same for each target sequence to be amplified if one set of target amplification primers are used, or the target amplification primers are designed to share have similar amplification characteristics for each target sequence to be amplified if multiple sets of target amplification primers are used. In one embodiment, both of the target amplification primers incorporate a means for detection that enables the amplified products to be detected and/or manipulated as described below. In an alternate embodiment, only 1 of the two target amplification primers incorporates a means for detection. In yet another alternate embodiment, only the RSP of the target amplification primers incorporates a means for detection. As used in this specification, a means for detection may be any element that is known in the art, such as a chemical element, an enzymatic element, a fluorescent element, or a radiolabel element. In one embodiment, the means for detection may be a fluorescent element, such as, but not limited to, a Cy-3 label. The fluorescent element may be directly conjugated to the super primer sequences or may be indirectly conjugated. In the case of indirect conjugation, the means for detection may be a biotin molecule (i.e. a chemical element) and the fluorescent element may be conjugated to an avidin or streptavidin molecule. The detection means may be manipulated as described below.

The target enrichment primers used in the Tem-PCR method are not used in a two-step PCR reaction as is commonly known in the art for nested primer applications. In Tem-PCR the target enrichment primers are used in a one step PCR reaction. Since the target enrichment primers are present in low concentrations, the target enrichment serve a target-enrichment purpose, rather than a target amplification purpose. The concentration of the target enrichment primers is not sufficient for exponential amplification of the target sequences. The target enrichment primers also serve to open up local template structures and therefore increase amplification sensitivity and/or efficiency. The exponential amplification of the sense target sequence is accomplished using the FSP and RSP.

As used in this specification, a "low concentration" when used to described the concentration of the target enrichment primers means a concentration of primers that is not sufficient for exponential amplification of the given target sequence(s) but is sufficient for target enrichment of the given target sequences. This low concentration may vary depending on the nucleotide sequence of the nucleic acid containing the target sequence to be amplified. In one embodiment, a concentration of target enrichment primers is in the range of 0.002 µM to less than 0.2 µM. In another embodiment, a concentration of target enrichment primers is in the range of 0.002 µM to 0.15 µM. In an alternate embodiment, a concentration of target enrichment primers is in the range of 0.002 µM to 0.1 µM. In yet another alternate embodiment, a concentration of target enrichment primers is in the range of 0.002 µM to 0.05 µM. Other concentration ranges outside those described above may be used if the nature of the nucleic acid sequence containing the target sequence to be amplified is such that concentrations of target enrichment primers below or above the ranges specified are required for target enrichment without exponential amplification. The various target enrichment primers may be used in different concentrations (i.e. ratios) or at the same concentration.

As used in this specification, a "high concentration" when used to described the concentration of the target amplification primers (FSP and RSP) means a concentration of primers that is sufficient for exponential amplification of the given target sequence. In one embodiment, a concentration of target amplification is in the range of 0.2 µM to 2.0 µM. In another embodiment, a concentration of target amplification primers is in the range of 0.2 µM to 1.0 µM. In an alternate embodiment, a concentration of target amplification primers is in the range of 0.2 µM to 0.8 µM. In yet another alternate embodiment, a concentration of target amplification primers is in the range of 0.2 µM to 0.4 µM. Other concentration ranges outside those described above may be used if the nature of the nucleic acid sequence containing the target sequence to be amplified is such that concentrations of target amplification primers below or above the ranges specified are required for exponential amplification. The super primers may be used in different concentrations (i.e. ratios) or at the same concentration.

As a general rule, a primer concentration in the range of 0.2 µM is generally used as a starting point for primer concentrations in order to achieve exponential amplification of a given target sequence. The target enrichment primers and the target amplification primers may be used in various ratios to each one another as discussed herein.

During the amplification process when two sets of target enrichment primers are used (FIG. 1A), the two sets of target enrichment primers will generate four possible amplified products, each containing the target sequence: $F_{out}/R_{out}$; $F_{out}/R_{in}$; $F_{in}/R_{out}$; and $F_{in}/R_{in}$. The super primer binding tag will be incorporated into any amplification product amplified using a target enrichment primer comprising the super primer binding tag, such as the $F_{in}$ or $R_{in}$ primer in FIG. 1A. However, the super primer binding tag is not useful for exponential amplification by the target amplification primers at this point since the super primer binding tag is identical to the sequence of the target amplification primers. In order to generate a super primer binding site, the amplification products containing me super primer binding tag must be amplified a second time in the opposite direction of the first amplification. The multiplex amplification protocol (discussed below) utilizes a multi-step procedure that allows for incorporation of the super primer binding tag into the amplification products. These steps are referred to as the target enrichment steps and the selective amplification steps. The target enrichment step may be used on its own or in combination with the selective amplification step. The target enrichment and selective amplification steps are optimized to provide conditions required for the low concentration target enrichment primers to hybridize to their hybridization targets for target enrichment. These steps create sufficient amplified product to serve as the basis for the exponential amplification procedure to be carried out by the target amplification primers. Therefore, at the low concentrations used, the target enrichment primers will generate target specific sequences with super primer binding tags incorporated therein. These super primer binding tags will generate super primer binding sequences for use by the target amplification primers for exponential amplification of the target sequences. The resulting amplified target sequences can be detected using target specific reporter (also referred to as detection) oligonucleotide as described below.

The result of the Tem-PCR amplification procedure is the specific enrichment of target sequences by the target enrichment primers, and the subsequent exponential amplification of the target sequences by the target amplification primers utilizing the super primer binding sites provided by the copying of amplification products containing the super primer binding tags. Since the exponential amplification of the each of the target sequences is carried out by one or more sets of target amplification primers the amplification conditions can be standardized and optimized taking into account only the target amplification primers. Therefore, incompatibility of the exponential amplification reaction conditions is not of concern as is the case for multiplex amplification methods currently known in the art.

The Tem-PCR amplification strategy produces decreased background since only the target amplification primers are present in high concentrations. As a result, the occurrence of primer dimmer formation and related phenomenon are reduced. Further adding to the reduced background, since only the super primers (or 1 of each set of super primers) are conjugated with a means for detection, even if primer dimmer formation occurs, it will not be detected by the reporter oligonucleotides. The reduced background will decrease the chance of false positive diagnosis.

The ratios of the target enrichment primers ($F_{out}$, $F_{in}$, $R_{out}$, and $R_{in}$) used in the Tem-PCR amplification method may be varied. Different pathogen genomes may have different target enrichment primer requirements. As discussed previously, some disease agents and secondary disease agents may have DNA genomes or RNA genomes (positive or negative strand). In addition, the concentration of target amplification primers may also be varied, especially if only 1 of the super primers is conjugated to a means for detection. Multiplex amplification where at least one of the target enrichment primers or super primers is used at a ratio different than 1:1 is referred to as asymmetric multiplex amplification.

In an experiment conducted using various target enrichment primer and target amplification primer ratios it was determined that increased amplification of the target sequences derived from negative strand RNA genomes occurred at a range of primer concentrations. In one embodiment, the concentration of $F_{out}$ was 1.0 to 8-fold greater than the concentration of the remaining target enrichment primers. An exemplary ratio would be 4:1:1:1 for $F_{out}:F_{in}:R_{out}:R_{in}$. For negative stranded RNA viruses, the amount of $F_{out}$ may be increased over the ratio of the remaining nested primers in order to provide for initial amplification of a positive RNA strand complementary to the genomic negative strand RNA. In one embodiment, increased amplification was observed when the concentrations of target amplification primers are about 1.25 to 32-fold greater than the concentration of $F_{out}$. An exemplary ratio would be 4:1:1:1:10:40 for $F_{out}:F_{in}:R_{out}:R_{in}:FSP:RSP$, respectively. The ratios of the individual target amplification primers can also be varied with respect one another. This asymmetric variation has been shown to provide increased sensitivity in the detection step (see Table 4). In one embodiment, the super primer incorporating the means for detection is added in a higher concentration that the other super primer. In one embodiment the RSP contains the means for detection and is added at a higher concentration. Increased amplification of the target sequences was observed when the concentrations of RSP were 1.25 to 16-fold greater than the concentration of FSP. An exemplary ratio would be 10:40 for FSP:RSP, respectively.

For amplification of target sequences from disease agents and secondary disease agents with positive stranded RNA genomes, additional primer ratios may be employed. In one embodiment, the concentration of $R_{out}$ was 1.0 to 8-fold greater than the concentration of the remaining nested primers. An exemplary ratio would be 1:1:4:1 for $F_{out}:F_{in}:R_{out}:R_{in}$. For positive stranded RNA viruses, the amount of $R_{out}$ may be increased over the ratio of the remaining target enrichment primers in order to provide for increased amplification the RNA strand containing the target sequence. In one embodiment, increased amplification was observed when the concentrations of target amplification primers are about 1.25 to 32-fold greater than the concentration of $R_{out}$. An exemplary ratio would be 1:1:4:1:10:40 for $F_{out}:F_{in}:R_{out}:R_{in}:FSP:RSP$, respectively. The ratios of the individual target amplification primers can also be varied with respect one another. This asymmetric variation has been shown to provide increased sensitivity in the detection step (see Table 4). In one embodiment, the super primer incorporating the means for detection is added in a higher concentration that the other super primer. In one embodiment the RSP contains the means for detection and is added at a higher concentration. Increased amplification of the target sequences was observed when the concentrations of RSP were 1.25 to 16-fold greater than the concentration of FSP. An exemplary ratio would be 10:40 for FSP:RSP, respectively.

For amplification of target sequences from disease agents and secondary disease agents with DNA genomes, additional primer ratios may be employed. In one embodiment, the concentration of the target enrichment primers are essentially equivalent. In an alternate embodiment, the concentration of one of $F_{out}$ or $R_{out}$ was 1.0 to 4-fold greater than the concentration of the remaining nested primers. An exemplary ratio would be 1:1:1:1 for $F_{out}:F_{in}:R_{out}:R_{in}$. In one embodiment, increased amplification was observed when the concentrations of target amplification primers are about 1.25 to 128-fold greater than the concentration of $R_{out}$. An exemplary ratio would be 1:1:1:1:10:40 for $F_{out}:F_{in}:R_{out}:R_{in}:FSP:RSP$, respectively. The ratios of the individual target amplification primers can also be varied with respect one another. This asymmetric variation has been shown to provide increased sensitivity in the detection step (see Table 4). In one embodiment, the super primer incorporating the means for detection is added in a higher concentration that the other super primer. In one embodiment the RSP contains the means for detection and is added at a higher concentration. Increased amplification of the target sequences was observed when the concentrations of RSP were 1.25 to 16-fold greater than the concentration of FSP. An exemplary ratio would be 10:40 for FSP:RSP, respectively.

In the embodiment where only 1 pair of target enrichment primers is utilized, the primers may be used at the different ratios discussed above (including the discussed target amplification primer ratios), with the ratios of the $F_{out}$ or $R_{out}$ primers above serving as the ratios for the corresponding primers in the 1 pair of target enrichment primers The concentration of the target enrichment primers are essentially equivalent.

Without being bound to alternate explanations, it is possible that as the concentration of target enrichment primers increase, target sequences are amplified without a means for detection and are able to complete for binding to the reporter oligonucleotide with the target sequences comprising a means for detection that are amplified by the FSP and/or RSP. The asymmetric amplification utilizing the target amplification primers may also increase amplification efficiency and sensitivity when the super primer containing the means for detection is used at a higher concentration because more amplification products containing the target sequence and the means for detection are produced and available for detection. Table 1 provides one set of exemplary ratios for the concentration of $F_{out}$, $F_{in}$, $R_{out}$, and $R_{in}$ as well as FSP and RSP.

As discussed above, the target amplification primers are used for the exponential amplification of each target sequence. The sequences of the target amplification primers are selected so they do not share obvious homology with any known GenBank sequences. In addition, the sequence of the target amplification primers is selected so they share a comparable Tm on binding to the super primer binding sites in the amplification products to provide efficient amplification reactions. Finally, the sequence of the target amplification primers may be selected such that their priming capabilities for thermal stable DNA polymerases maybe superior to the target enrichment primers which are specific for each target sequence to be amplified.

The multiplex amplification is performed as per standard procedures known in the art. In one embodiment, RT-PCR or PCR is used as the amplification step. The PCR enzyme may be an enzyme with both a reverse transcription and polymerase function, such as Taq polymerase. Furthermore, the PCR enzyme may be capable of "hot start" reactions as is known in the art. The conditions for RT-PCR or PCR are known in the art. However, the applicants have produced an optimized set of RT-PCR and PCR conditions that are designed for use with the TemPCR method. The exact times and temperatures may be varied to accomplish the objects as discussed below as would be known to one of skill in the art. In one embodiment, the RT-PCR or PCR conditions are as follows. The method below comprises a set of first amplification conditions for a first amplification reaction that serves a target enrichment function and a second amplification reaction that comprises a target amplification function. The samples containing the reagents for amplification were placed in a thermocycler programmed as follows: (i) reverse transcription—30 minutes at 50° C.; (ii) initial PCR activation—15 minutes at 95° C.; (iii) first amplification reaction comprising a first 3-step cycling (target enrichment)—0.5 to 1 minute at 92-94° C., 1 to 2.5 minutes at 50-55° C. and 0.5 to 1 minute at 70-72° C.; for at least 2 complete cycles, preferably for 10-15 complete cycles; (iv) second amplification reaction comprising a second 3-step cycling (target amplification)—15 to 30 seconds at 92-94° C., 15 to 30 seconds at 50-55° C. and 15 to 30 second at 70-72° C.; for at least 2 complete cycles, preferably for 10-40 complete cycles; and (v) final extension—3 minutes at 72° C.

Step (i) allows for the reverse transcription reaction to occur in the cases where the nucleic acid of the disease agent and/or secondary disease agent is not DNA. Step (ii) allows for activation of the PCR enzyme function. This technique is known as "hot start" PCR, where at lower temperatures (50° C.) the PCR enzyme function is only competent to carry out the reverse transcription reaction, but at higher temperatures the PCR enzyme function is capable of polymerase function. Incubation of the PCR enzyme function is required to relieve the inhibition of the polymerase function. The first amplification in step (iii) is designed to allow the target enrichment primers to hybridize to their targets and prime the target enrichment step. As can be seen, additional time is allowed for the target enrichment primers to hybridize to their targets (2.5 minutes at 50-55° C. as compared to 15 seconds 50-55° C. in step (iv)). Increased times are used since the target enrichment primers are used at lower concentrations. The target amplification reaction in step (iv) is the exponential amplification phase using the target amplification primers (which are at high concentration). Since the target amplification primers are present at high concentrations, increased hybridization times between the target amplification primers and targets are not required. Step (v) is the final extension step to generate full double stranded amplification products. Step (v) is optional and need not be included.

In an alternate embodiment, the RT-PCR or PCR conditions are as follows. The reaction tubes containing the reagents for amplification were placed in a thermocycler programmed as follows: (i) reverse transcription—30 minutes at 50° C.; (ii) initial PCR activation—15 minutes at 95° C.; (iii) first amplification reaction comprising a first 3-step cycling (target enrichment)—0.5 to 1 minute at 92-94° C., 1-2.5 minutes at 50-55° C. and 0.5 to 1 minute at 70-72° C.; for at least 2 complete cycles, preferably for 10-15 complete cycles; and a second 2-step cycling (selective amplification)—15 to 30 seconds at 92-94° C., 1 to 2 minutes at 70-72° C.; for at least 2 complete cycles, preferably 4-8 complete cycles; (iv) second amplification reaction comprising a third 3-step cycling (target amplification)—15 to 30 seconds at 94° C., 15 to 30 seconds at 50-55° C. and 15 to 30 second at 72° C.; for at least 2 complete cycles, preferably for 10-40 complete cycles; and (v) final extension—3 minutes at 72° C.

In this embodiment the functions of the various steps are as described above. However, the first amplification reaction comprises an additional 3-step cycling procedure has been added to increase the production of amplification products incorporating the super primer binding tags, which ultimately give rise to amplification products containing the super primer binding sites. In the added 3-step cycling procedure, the hybridization temperature in increased to 70-72° C. (as compared to 50-55° C. in step (iii)). The hybridization time is also increased as discussed above to give the low concentration target enrichment primers an opportunity to hybridize to their targets. This increased hybridization temperature endures that only target enrichment primers of a certain length are stable enough to hybridize to their targets. In this embodiment, the $F_{out}$ and $R_{out}$ primers are selected to have a length of 20 nucleotides or less, while the $F_{in}$ and $R_{in}$ primers (which in this embodiment comprise the super primer binding tags) are at least 30 to 40 nucleotides in length. Therefore, the $F_{out}$ and $R_{out}$ primers are not thermally stable at 70-72° C., meaning they will not hybridize to their targets. However, the increased length of the $F_{in}$ and $R_{in}$ primers ensures that these primers are thermally stable at 70-72° C. and will hybridize to their targets. In the selective amplification steps, the $F_{in}$ and $R_{in}$ primers hybridize along their entire length (40 nucleotides) to complementary sequences in the initial set of amplification products created by the amplification in the opposite direction of initial amplification products incorporating the $F_{in}$ and $R_{in}$ primers. (in the target enrichment step, the $F_{in}$ and $R_{in}$ primers The $F_{in}$ and $R_{in}$ primers produce an increased amount of amplification products containing the super primer binding tags, which increases the amount of exponential amplification in step (v). Therefore, step (iv) is a selective amplification step biased towards producing amplification products containing the super primer binding tags. This selective amplification is accomplished without the need to engineer higher GC content or without the need to use modified nucleotides to increase thermal stability. The amplification products of step (iv) are then subject to exponential amplification as described above.

Multiplex Detection

A robust target sequence multiplex amplification method provides the basis for a sensitive and specific multiplex detection. The multiplex detection method used in MAS complements the multiplex amplification to provide balanced sensitivity and specificity in detection of amplified target sequences. Sensitivity and specificity are important issues for a successful diagnostic test or differential diagnostic test.

The multiplex detection method for use in MAS can be either a direct detection or an indirect multiplex detection method. The nature of the target sequences will in part determine whether direct or indirect detection is used. For example, if the target sequences do not share extensive homology with one another, the required sensitivity and specificity may be obtained by directly hybridizing the reporter oligonucleotide to the target sequences. For example, in diagnostic test for a disease agents or differential diagnostic test for disease agents and at least one secondary disease agent, the multiplex amplification may be designed so that each of the target sequences amplified from the disease agent and the secondary disease agent do not share extensive homology so that direct detection may be used. However, if the target sequences amplified do share extensive homology with one another, additional steps may be incorporated in the multiplex detection step to add additional discrimination between the homologous sequences so that the required sensitivity and specificity are obtained. For example, in a diagnostic test to determine the presence of one or more single nucleotide polymorphisms in the alleles of an individual, direct hybridization may not be able to provide the required allelic discrimination required to specifically detect target sequences differing by only one nucleotide. In this case, an indirect detection method may be used to add additional discriminatory power.

Figure 2:
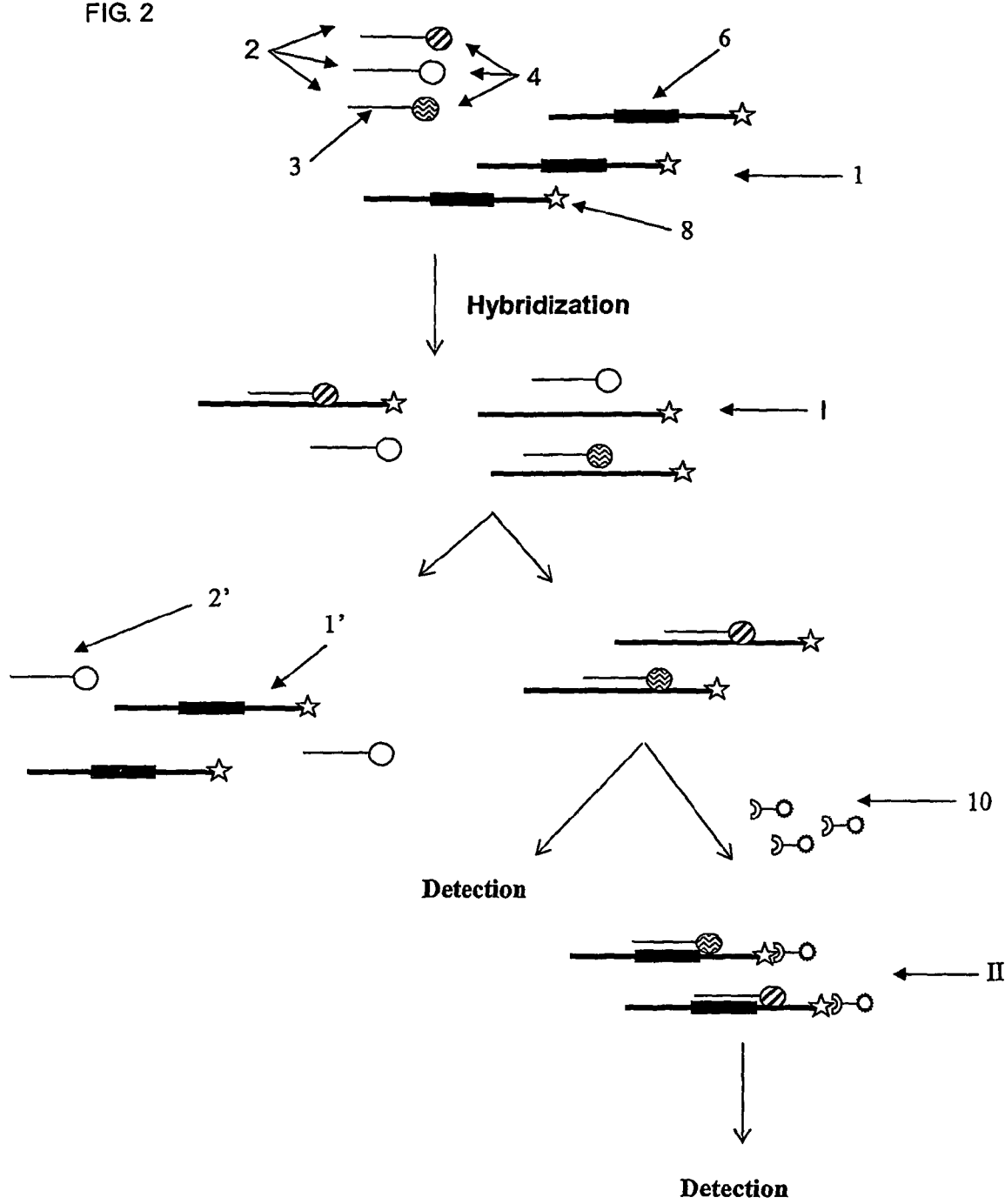
FIG. 2 is an illustration of one embodiment of the direct detection methodology.

FIG. 2 shows an embodiment of the direct detection method. Amplified nucleic acid (1) containing a target sequence (6) from a multiplex amplification reaction is provided for detection (the amplification process may be the Tem-PCR process described herein). Reporter oligonucleotides (2) comprising a hybridization domain (3) specific for a known target sequence (6) are provided and are conjugated to a means for first signal generation (4). The means for first signal generation is capable of producing a detectable first signal. The means for first signal generation (4) may be varied depending on the technology platform employed in the detection step. For example, if the LUMINEX® platform (a microsphere based multiplex detection system) is employed as the technology platform in the detection step, the means for first signal generation (4) may be an internally color coded, spectrally addressable microsphere as shown in FIG. 2. Variations to the direct detection methods described below are described in co-pending U.S. application Ser. No. 10/284,656, with the implementation of such variations being obvious to one of ordinary skill in the art.

The reporter oligonucleotides (2) are designed to hybridize specifically to a specific target sequence (6) provided by the multiplex amplification step discussed above. The specificity of the hybridization between the reporter oligonucleotide (2) and the target sequence (6) can be adjusted by increasing or decreasing the length of the hybridization domain (3) of the reporter oligonucleotide. In general, a shorter hybridization domain (3) will give increased specificity and differentiation as a mismatch between the target sequence (6) and the hybridization domain (3) will have a significant impact on the hybridization efficiency. A longer hybridization domain (3) will provide less specificity but greater hybridization efficiency and therefore increased sensitivity. The nature of the target sequence (6) will influence the composition of the hybridization domain (3). One of ordinary skill in the art would be able to alter the parameters of the hybridization domain (3) to achieve the desired specificity and sensitivity of binding of the hybridization domain (3) to the target sequence (6). In one embodiment, the hybridization domain (3) is 10 to 50 bp in length. In an alternate embodiment, the hybridization domain (3) is 20-40 bp in length. In yet another alternate embodiment the hybridization domain (3) is 15 to 25 bp in length.

Each reporter oligonucleotide (2), which specifically hybridizes to a known target sequence (6) via the hybridization domain (3), will be associated with a known means for first signal generation (4) (such as a color coded bead). Therefore, by determining the identity of the means for first signal generation (4), the identity of the target sequence (6) can be determined, and therefore the identity of the disease agent or secondary disease agent can be determined.

Amplified nucleic acid (1) containing a target sequence (6) may be denatured before or during the multiplex detection step, if desired. Denaturation is not required. The TemPCR amplification reaction using asymmetric amplification conditions (such as RSP being present in greater concentrations that FSP, such as a 40:10 ratio) produces sufficient single stranded amplification products for the detection reaction that denaturation is not a required step. Denaturation, in this and other steps referred to in this disclosure, may occur by heating to a sufficient temperature or by chemical means (such as, but not limited to, the addition of agents such as 5N NaOH). For the following embodiment, denaturation of the amplified nucleic acid (1) containing a target sequence (6) was not used. However, the principles embodied in the following steps will not differ if the denaturation step is added.

The reporter oligonucleotides (2) are added to the denatured amplified nucleic acid (1) in appropriate hybridization buffer (such as 1×TMAC or 1×TE). The addition of the reporter oligonucleotides (2) may occur before or after denaturation (if employed). The reporter oligonucleotides (2) bind the target sequences (6) on the amplified nucleic acid (1) through the hybridization domain (3) forming a nucleic acid-reporter oligonucleotide complex (I). Hybridization conditions as are known in the art, such as by incubation at 52° C. for 15 minutes, may be used. After hybridization is complete, complex I is isolated, such as by centrifugation, and the unbound reporter oligonucleotides (2') and unbound amplified nucleic acid (1') are removed. Complex 1 may then be subject to detection using an appropriate detection platform. In one embodiment, the means for first signal generation (4) is an internally color coded spectrally addressable bead (obtained from Luminex Corporation, Austin, Tex.) and the LUMINEX® platform (a microsphere based multiplex detection system) is used for detection. The LUMINEX® platform (a microsphere based multiplex detection system) stimulates the means for first signal generation (4) to produce a detectable first signal. The first signal is recorded and interpreted. The means for first signal generation (4) and the produced first signal are used to determine the identity of the target sequence (6) bound by the reporter oligonucleotide (2). Once the target sequence (6) has been identified, the identity of the disease agent or secondary disease agent detected is known.

The complex (II) may then be analyzed using an appropriate platform. In one embodiment, the means for first signal generation (4) is an internally color coded spectrally addressable bead (obtained from Luminex Corporation, Austin, Tex.) and the means for second signal generation (10) is a fluorescent PE label. In this embodiment, the LUMINEX® platform (a microsphere based multiplex detection system) is used for detection. The LUMINEX® platform (a microsphere based multiplex detection system) stimulates the means for first (4) second (10) signal generation to produce a detectable first and second signal, respectively. The first and second signal generating means are selected such that the first and second signals can each be detected in presence of the other. The first and second signal are recorded and interpreted. The means for first signal generation and the produced first signal are used to determine the identity of the target sequence (6) bound by the reporter oligonucleotide (2). The means for second signal generation (10) and the second signal are used to confirm the presence of the target sequence (6) in combination with the reporter oligonucleotide (2) (to prevent signal generation from any free reporter oligonucleotide (2)). Once the target sequence (6a) has been identified, the identity of the disease agent or secondary disease agent detected is known. However, it should be noted that complex I may be subject to detection as described above Additional technology platforms may be used in the direct detection step as well. In an alternate embodiment, the first signal generating means on the reporter oligonucleotide may produce a detectable physical first signal when placed in an appropriate apparatus for detection and analysis. The physical signal may be a color change, an emission of a given wavelength of light upon excitation or a change in the electrical properties, such as conductivity, or a change in the electromagnetic or chemical properties. Other physical signals may also be used. In one embodiment, the means for first signal generation may be spatial in nature, such as location on a solid support. For example, reporter oligonucleotide may be spatially resolved at a known location on the collecting means such as a chip or other solid support. Therefore, the first signal is spatial in nature. When the amplified products containing the target sequence hybridize to a reporter oligonucleotide, the binding may be determined by the presence of the second signal generated by the second signal generating means on the amplified nucleic acid. By detecting the spatial location (first signal) of the second signal, the identity of the target sequence and the disease agent/secondary disease agent is determined. In an alternate embodiment, the reporter oligonucleotide may be coupled to an additional first signal generating means so that two first signals are produced, one spatial and one non-spatial. Therefore, the second signal produced by the second signal generating means will signal binding of the target nucleic acid to the reporter oligonucleotide. In an alternate embodiment, the biding of the target sequence to the reporter oligonucleotide may produce a detectable change in the characteristics of the reporter oligonucleotide (including but not limited to changes in electrical properties such as conductivity). This change in characteristics would then serve as the second signal.

In one embodiment of the indirect detection protocol, a novel method termed ROCASH (Reporter Oligo Capturing After Specific Hybridization) is used. The ROCASH method is described in co-pending U.S. application Ser. No. 10/284,656, which is hereby incorporated by reference as if fully set forth herein. For sake of clarity, one embodiment of the ROCASH method using the LUMINEX® X-Map technology is described (a microsphere based multiplex detection system). Other methods of indirect detection may also be used as is known in the art. It is understood that variations of the ROCASH method may be incorporated as described in the co-pending U.S. application Ser. No. 10/284,656. Unlike the prior art methods, in the ROCASH method the specificity of hybridization between a reporter oligonucleotide and the target sequence and the sensitivity of the detection of the target sequence are provided by different nucleic acid sequences of the reporter oligonucleotide hybridizing in different steps of the ROCASH method. Therefore, the conditions for these critical steps may be optimized independently of each other to provide for increased specificity and sensitivity in the detection step.

The LUMINEX® xMAP technology (a microsphere based multiplex detection system) and related technologies are described in the art and in U.S. Pat. Nos. 6,524,473, 6,514,295, 6,449,562, 6,411,904, 6,366,354, 6,268,222, 6,139,800, 6,057,107, 6,046,807 and 5,736,330. The xMAP technology uses a plurality of internally color-coded microspheres covalently bound to target specific capturing reagents (turned cRTs, as defined below). Such capturing reagents may be oligonucleotides (as in the case of cRTs described below), but may also be polypeptides or chemical moieties designed to interact specifically with the region tags. When alternate capturing reagents are used, the region tags on the reporter oligonucleotides may altered to provide a complementary binding partner. The internal color coding generates a unique signal for each set of beads on excitation by the LUMINEX® platform (a microsphere based multiplex detection system).

The ROCASH method may be considered to comprise two primary components: (i) a reporter oligonucleotide; and (ii) a means for collection. The reporter oligonucleotides are designed to bind specifically to the target sequence provided by the multiplex amplification step discussed above. The reporter oligonucleotides comprise a hybridization domain of variable length designed to hybridize to the target sequence (see discussion above regarding the effect of the length of the hybridization domain on specificity and sensitivity), a nucleic acid sequence termed the region tag for hybridization to the means for collection, and a means for first signal generation. In one embodiment, the region tags on the reporter oligonucleotides are unique for each hybridization domain. In other words, a reporter oligonucleotide having a hybridization domain that binds to target sequence "A" and a reporter oligonucleotide having a hybridization domain that binds to target sequence "B" will have different region tags. The means for collection comprises and a plurality of capturing reagents, in this embodiment termed cRTs (complementary region tags) and a means for second signal generation, cRTs are nucleic acid sequences that are complementary to the region tags contained in the reporter oligonucleotides. The means for first and second signal generation may vary depending on the nature of the technology employed in the detection platform. When using the LUMINEX® X-Map technology (a microsphere based multiplex detection system), the means for first signal generation may be a fluorescent tag, such as PE or Cy-3, and the means for second signal generation may be an internally color coded, spectrally addressable microsphere. Through interaction of the region tags of the reporter oligonucleotide and the cRTs of the means for collection, each reporter oligonucleotide (which is specific for a known target sequence by virtue of the hybridization domain) will be associated with a known means for second signal generation (such as a color coded bead obtained from Luminex Corporation, Austin, Tex.). Therefore, by determining the identity of the means for second signal generation, the identity of the target sequence can be determined, which will allow the identification of the disease agent or secondary disease agent. Therefore, the specificity is achieved by the hybridization between the hybridization domain of the reporter oligonucleotide and the target sequence (note that specificity may be altered by decreasing or increasing the length of the hybridization domain) and the sensitivity is determined by the hybridization between the region tag of the reporter oligonucleotide and the cRT of the means for collection. A means for purification may also be used that is designed to interact with the amplified nucleic acid sequences and aids in the removal of the unused amplified target nucleic acids as discussed below.

Figure 3:
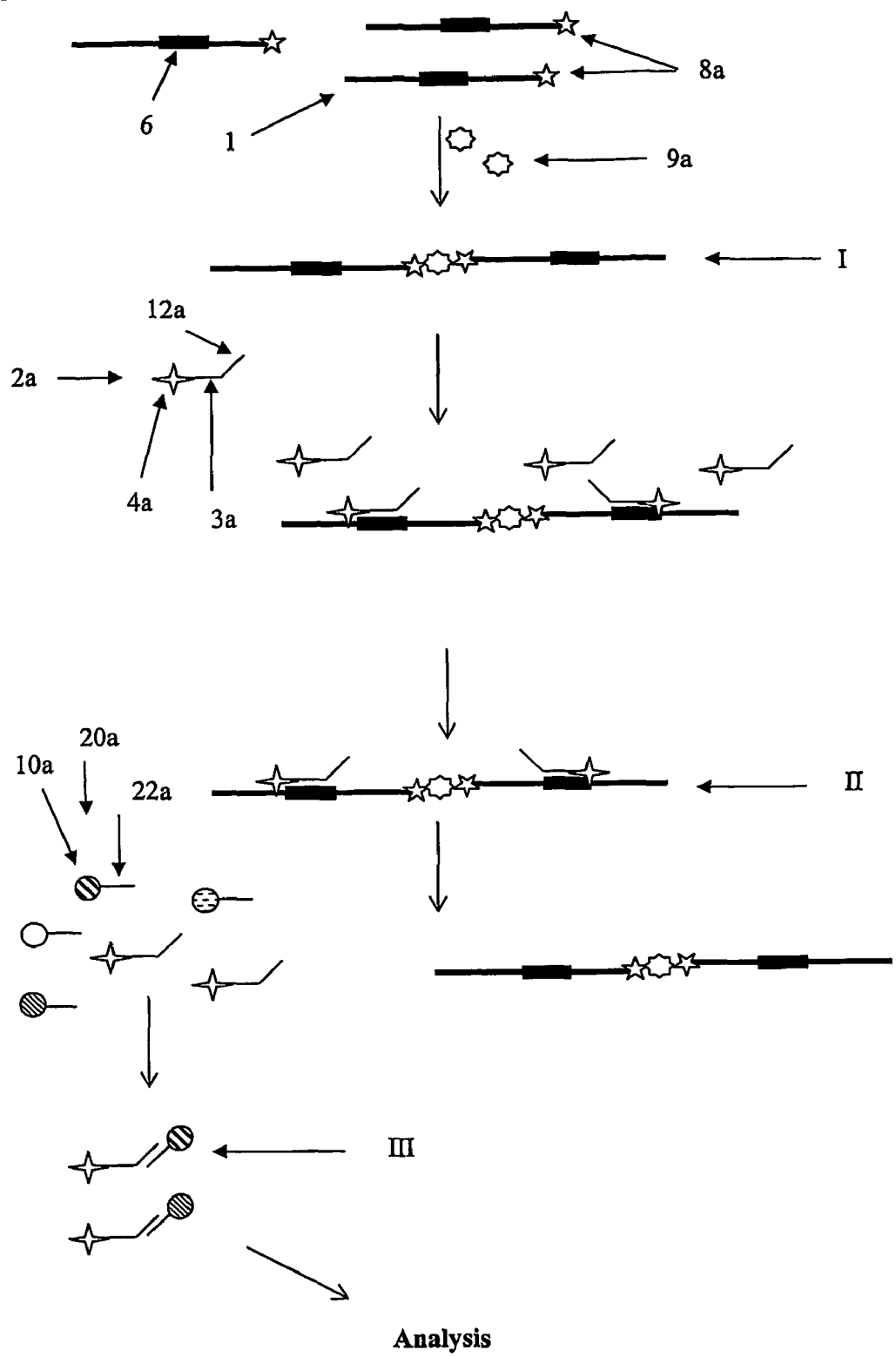
FIG. 3 is an illustration of one embodiment of the indirect detection methodology.

One embodiment of the ROCASH procedure is illustrated in FIG. 3. Amplified nucleic acid (1a) containing a target sequence (6a) from a multiplex amplification reaction is provided for detection (the amplification process may be the Tem-PCR process described herein). The amplified nucleic acid (1a) containing the target sequence (6a) may be denatured if desired. The denaturation step is optional however. FIG. 3 shows the amplified nucleic acid (1a) after a denaturation step. As discussed above, the reverse strand of the amplified nucleic acid will contain a means for detection (8a) provided by at least one of the FSP or RSP. This means for detection (8a) may be a biotin molecule attached to the FSP and/or the RSP or other such means as is known in the art as discussed above. The means for purification (9a) is selected to interact with the means for detection (8a). In one embodiment, the means for purification (9a) is a magnetic bead (such as the Dynal270 magnetic bead) conjugated to streptavidin and the means for detection (8a) is a biotin label. The means for purification (9a) is added to the amplified nucleic acid (1a) where it binds the means for detection (8a) to form a nucleic acid-means for purification complex (complex I). Complex I is washed to remove the unbound nucleic acid and the remaining components and isolated using separation techniques known in the art and compatible with the means for purification. In the case where the means for purification is a magnetic bead, magnetic separation techniques may be used. Hybridization buffer, such as 1× TMAC or 1× TE, is added to the complex I to prepare for hybridization.

The reporter oligonucleotides (2a) are then added to the complex I. The reporter oligonucleotides may be added at prior steps, however, if desired, either before or after the denaturation of the amplified nucleic acid. The reporter oligonucleotides (2a) bind the target sequences through the hybridization domain (3a) forming a means for purification-nucleic acid-reporter oligonucleotide complex (complex II). The reporter oligonucleotides (2a) also comprise a region tag (12a) and a means for first signal generation (4a). Hybridization may occur as is known in the art, such as by incubation at 52° C. for 15 minutes. After binding, complex II may be washed (such as in warm 1×SSC) and isolated using appropriate separation techniques as discussed above. After removal of unbound reporter oligonucleotides, complex (II) is subject to denaturation conditions to release the reporter oligonucleotide (2a) from target sequences (6a). The nucleic acid-means for purification complex is removed by appropriate separation techniques as discussed above.

The means for collection (20a) is mixed with the reporter oligonucleotides (2a) remaining in solution. The means for collection comprises a cRT (22a) and a means for second signal generation (10a). The cRT (22a) of the means for collection (20a) interacts with the region tags (12a) of the reporter oligonucleotides forming a collecting means-reporter oligonucleotide complex (complex III). The cRTs (22a) and region tags (12a) are selected so that each cRT/region tag complementary pair has a similar $T_m$ for binding to one another. Therefore, the hybridization conditions for each region tag (12a) to it complementary cRT (22a) are universal. This allows for increased sensitivity of detection, particularly in a multiplex detection setting, since one set of hybridization conditions are used. Hybridization conditions as described above may be used as well as other hybridization conditions as are known in the art. Complex (III) is then isolated and analyzed using an appropriate detection platform In one embodiment, the means for first signal generation (4a) is a fluorescent PE label and the means for second signal generation (10a) is an internally color coded spectrally addressable bead (provided by Luminex Corporation, Austin, Tex.). In this embodiment, the LUMINEX® platform (a microsphere based multiplex detection system) is used for detection. The LUMINEX® platform (a microsphere based multiplex detection system) stimulates the means for first (4a) second (10a) signal generation to produce a detectable first and second signal, respectively. The first and second signal are recorded and interpreted. The first and second signal generating means are selected such that the first and second signals can each be detected in presence of the other. The means for second signal generation and the produced second signal are used to determine the identity of the target sequence (6a) bound by the reporter oligonucleotide (2a). The means for first signal generation (10a) and the second signal are used to indirectly confirm the presence of the target sequence (6a) (to prevent signal generation from any free means for collection 10a). Once the target sequence (6a) has been identified, the identity of the disease agent or secondary disease agent detected.

Differential Diagnosis of Severe Acute Respiratory Syndrome (SARS) Using an Embodiment of MAS Below are several examples of the MAS utilizing the teaching of the present disclosure to provide a differential diagnostic assay for SARS (in these examples SARS-CoV). In this example, SARS is the disease agent and the secondary disease agent includes one or more of the following: respiratory syncytial virus (RSV) A and B, parainfluenza virus (PIV) 1 and 3, influenza (INF) A and B, adenovirus strains (ADV), C. pneumoniae and M. pneumoniae, enterovirus (ENT), and enterovirus types such as coxsackie virus A (CVA), coxsackie virus B (CVB), rhinovirus (RhV), and echovirus (EV). As discussed above, these examples are provided as exemplary in nature and are not meant to limit the present disclosure to the disclosed differential diagnosis as other target sequences from other disease agents and secondary disease agents may be amplified and detected.

Tables 2 and 3 lists the sequence of the target enrichment primers (designated $F_O$, $F_I$, $R_O$, and $R_I$ for $F_{out}$, $F_{in}$, $R_{out}$ and $R_{in}$, respectively, as such terms are defined herein) used in the TemPCR method to amplify target sequences from the disease agent and secondary disease agents, as well as the nucleic acid sequence of the reporter oligonucleotide (designated De). In Tables 2 and 3 the $F_i$ and $R_i$ primers contained the super primer binding tag. Table 2 also provides the GenBank accession numbers for the nucleic acid sequence of the disease agent and secondary disease agents as well as the region of nucleic acid bound by the primers and the reporter oligonucleotide. The sequence of the target amplification primers (FSP and RSP) are provided at the bottom of Tables 2 and 3.

In these examples, three target sequences from the SARS viral genome were amplified and detected. The SARS virus is known to have a high mutation rate. If mutations occur at the primer binding sites or at the detection hybridization site, a false negative result may be introduced. Detecting three targets from the SARS pathogen increases detection sensitivity and reduces false negative results. For the secondary disease agents, one region of nucleic acid from each of the respective nucleic acids was amplified and detected. The target enrichment primers listed in Table 2, in some cases, may be used to detect multiple strains of a pathogen. For example, the target enrichment primers used to amplify influenza A produce amplified nucleic acid containing a target sequence sufficient for the detection and differentiation (using the appropriate detection oligonucleotides) of a variety of strains, including, but not limited to, H1N1, H1N2, H2N2, H3N2, H4N6, H5N1 and H9N2. The target enrichment primers used to amplify influenza B produce amplified nucleic acid containing a target sequence sufficient for the detection and differentiation (using the appropriate detection oligonucleotides) of a variety of strains, including but not limited to, Lee40, Memphis 97, Saya 99 and Taiwan 99. The primers used to amplify the adenovirus produce amplified nucleic acid containing a target sequence sufficient for the detection and differentiation (using the appropriate detection oligonucleotides) of adenovirus strains 3, 4, 7, 14, and 21. In each of the above cases, detection oligonucleotides specific for each strain can be used in the detection step to identify a particular strain. The RSP is labeled with a means for detection, such as biotin (other labeling molecules may be used as discussed above).

The target enrichment primers listed in Table 3 also, in some cases, may be used to detect multiple strains of a pathogen. Table 4 shows the genes amplified from the various pathogens by the target enrichment primers shown in Table 3. A nonstructural gene (NS) was selected as the amplification from the Influenza A viruses. Conserved regions were selected for the design of the 4 target enrichment primers and produce amplified nucleic acid containing a target sequence sufficient for the detection and differentiation (using the appropriate detection oligonucleotides) of a variety of strains including, but not limited to, H1N1, H1N2, H2N2, H3N2, H3N8, H4N6, H4N8, H5N1, H5N2, H5N3, H6N1, H6N2, H6N4, H7N1, H7N2, H7N3, H7N7, H7N8, H9N2, H10N5, H11N1, H11N8, and H11N9 (which includes the currently circulating avian influenza A strain, H5N1). A nonstructural gene was also selected as the target for amplification and detection of Influenza B virus. There are at least 51 known serotypes of adenoviruses. Conserved regions in the hexon gene were selected for the design of the series of target enrichment primers and produce amplified nucleic acid containing a target sequence sufficient for the detection and differentiation (using the appropriate detection oligonucleotides) of a variety of strains including, but not limited to, Serotypes 3, 4, 7, 14 and 21 (which includes those serotypes commonly associated with respiratory infections). The detection oligonucleotide ADV3-3De detects strains 3, 7 and 21, ADV4-3De detects strain 4 and Adv14-3De detects strain 14. Conserved sequences from the 5' UTR region of various enteroviruses species and family members were selected for amplification. Enteroviruses and rhinoviruses are members of the Picornaviridae family. Enteroviruses also include different genera such as coxsackie viruses and echoviruses. These viruses are all associated with respiratory infections. For the detection of various members of the enterovirus class, a series of target enrichment primers were designed that produces amplified nucleic acid containing a target sequence sufficient for the detection and differentiation (using the appropriate detection oligonucleotides) of a variety of strains of: rhinovirus including, but not limited to, Ts, 1a, 1b, 2, 9, 14, 15, 16, 39, 49, 50, 85, and 89; coxsackie virus A, including, but not limited to, A21 and A24; coxsackie virus B including, but not limited to, B4 and B5; and echovirus including, but not limited to, 11, 20, and 25. The detection oligonucleotide Rhv2 is specific for the detection of the rhinovirus, while the detection oligonucleotide CVE2 detects coxackie virus A and B and echovirus.

Conserved sequences from the nucleocapsid protein gene (N gene) were selected amplification from the Parainfluenza type 1 and 3 viruses. Nonstructural gene sequences were selected as targets for Respiratory syncytial viruses A and B. To reduce background amplification and false positive detections, rRNA genes were not selected for amplification from the bacteria species listed. Instead, the cytadhesin P1 gene from *Mycoplasma pneumoniae*, and the *Uridine Kinase* gene from *Chlamydia pneumoniae* were selected for amplification. The RSP is labeled with a means for detection, such as biotin (other labeling molecules may be used as discussed above).

The primer sequences used in the present detection method may be varied as discussed in more detail above. In addition, other agents may be included for detection in the method disclosed by designing primers specific for the agents. Such modification may be desirable if new agents are discovered that cause a SARS-like disease state or if additional SARS variants are isolated.

EXAMPLE 1

In this example, nucleic acid sequences from each disease agent and the secondary disease agents were obtained and isolated as described herein. The nucleic acid from each agent was amplified by the Tem-PCR method described herein. The nucleic acid for each agent was placed in a separate reaction tube and the complete mix of primers specified in Table 2 was added along with reagents for RT-PCR. A separate reaction was carried out for each of the three primer ratios specified in Table 5 for each agent. While any procedure known in the art for RT-PCR may be used, the following procedure was used in the example. A master RT-PCR mix was prepared containing 5× RT-PCR buffer, deoxy nucleoside triphosphate (dNTP) mix (containing 400 uM of each dNTP), the complete mix of primers shown in Table 2 at the ratios specified in Table 5, and RT-PCR enzyme preparation. An RNAse inhibitor may also be added at a concentration of 5-10 units/reaction if desired. The nucleic acid sequences or portions thereof containing the target sequences from each disease agent and secondary disease agent sufficient for amplification were added to individual reaction tubes containing the RT-PCR master mix. A RT-PCR blank was prepared by adding RNAse free water to one reaction tube in place of nucleic acid template. The reaction tubes were placed in a thermocycler programmed as follows: (i) reverse transcription—30 minutes at 50° C.; (ii) initial PCR activation—15 minutes at 95° C.; (iii) first amplification reaction comprising a first 3-step cycling (target enrichment)—1 minute at 94° C., 2.5 minutes at 55° C. and 1 minute at 72° C. for 10 complete cycles; (iv) second 3-step cycling (target amplification)—30 seconds at 94° C., 15 seconds at 55° C. and 15 second at 72° C. for 40 complete cycles; and (v) final extension—3 minutes at 72° C.

An aliquot of the amplified products were subject to detection using the direct detection method as described above and illustrated in FIG. 2. In this example, detection oligonucleotides (as listed in Table 2) specific for a target sequence amplified in each agent to be detected were coupled to microspheres (obtained from Luminex Corporation, Austin, Tex.). An aliquot of the amplified products were added, in separate tubes, to a reaction mixture containing 1×TE, hybridization buffer and an amount of each detection oligonucleotide sufficient to generate a detectable signal. In this example, detection oligonucleotide for each agent in Table 2 was present in each reaction containing the amplified nucleic acid products. For the detection oligonucleotide negative control, 1×TE was added in place of the amplified products. The samples were immediately placed at 52° C. for 15 minutes for hybridization between the detection oligonucleotide and the target sequence. The samples were centrifuged to remove unbound detection oligonucleotide and nucleic acid to which the detection oligonucleotides had not bound. The samples were then subject to detection using the LUMINEX® platform (a microsphere based multiplex detection system). The LUMINEX® platform (a microsphere based multiplex detection system) stimulated the microsphere conjugated to the detection oligonucleotide (the first signal generating means) to produce a detectable signal. In this example, a second means for detection was not included, however, a second signal may be incorporated as discussed above.

The results are presented in Table 3. The rows represent the identity of the disease agent or secondary disease agent whose nucleic acid was used in the initial amplification reaction and the ratio of the primers used in the amplification step. The columns represent the detection oligonucleotides used in the detection step. For example, row 5 (designated RSVB 4:1:1:1:8:16) indicates the nucleic acid of respiratory syncytial virus type B was used in the amplification reaction and the nested primers and super primers were used in a ratio of 4:1:1:1:8:16. Row 2 (designated RSVB) indicated the detection oligonucleotide specific for the respiratory syncytial virus type B target sequence was used in the detection step. Column 1 (designated Lum Blank) represents a detection oligonucleotide negative control where the amplified products omitted. Rows 3-5 (designated Blank 4:1:8:16, Blank 4:1:8:24 and Blank 4:1:8:32, respectively) represent amplification negative controls where the specific nucleic acid sequence was omitted but the primers for amplification of each specific target sequence were included at the indicated ratios.

As can be seen in Table 4, the detection oligonucleotides specific for a given disease agent or secondary disease agent specifically bound to the nucleic acid from that disease agent or secondary disease agent in the presence of multiple amplified target sequences. This result indicates that the target enrichment primers amplified the correct target nucleic acid sequence in the presence of multiple primer sets not specific for the target sequence and that the target amplification primers (FSP and RSP) function correctly to amplify the target sequence as described and the appropriate detection oligonucleotides are capable of hybridizing to the target sequence being detected. The detection oligonucleotide negative control and amplification negative controls provided background readings and showed no excessive background signal in all samples tested.

As one example, the detection oligonucleotide specific for RSVB bound specifically to the target sequences derived only from RSVB and no other agents. In addition, the level of detection increased as the concentration of RSP was increased, indicating that asymmetric amplification can increase sensitivity of the detection step. Furthermore, in the case of adenovirus, Table 4 indicates that the target enrichment primers and target amplification primers amplified the correct adenovirus target sequence and that the specific detection oligonucleotides were capable of discriminating between the adenoviral strains.

EXAMPLE 2

In this example, nucleic acid sequences from each disease agent and the secondary disease agents were obtained and isolated as described herein. The nucleic acid from each agent was amplified by the Tem-PCR method described herein. The nucleic acid for each agent was placed in a separate reaction tube and the complete mix of primers specified in Table 3 was added along with reagents for RT-PCR. The RT-PCR conditions were as described in Example 1 above. The primer rations used in this example were 1:1:1:1:10:40 ($F_{out}$:$F_{in}$:$R_{in}$:$R_{out}$:FSP:RSP).

The detection of the amplified products containing the target sequence was carried out as described for the direct detection methodology using beads as described in Example 1 (obtained from Luminex Corporation, Austin, Tex.). Detection oligonucleotides for each agent listed in Table 3 were added to each detection reaction.

Table 6 shows the results of this experiment using the target enrichment and target amplification primers disclosed in Table 3. The rows represent the identity of the disease agent or secondary disease agent whose nucleic acid was used in the initial amplification reaction and the ratio of the primers used in the amplification step. The columns represent the detection oligonucleotides used in the detection step. In this example, sample number 1 is a RT-PCR Blank comprising a mixture of target enrichment and target amplification primers and detection oligonucleotides conjugated to beads (obtained from Luminex Corporation, Austin, Tex.) were hybridized to the RT-PCR reaction that did not include template. The background signals are used to determine the cut-off values for a positive reaction. In a multiplexed system, such as the MAS utilizing TemPCR, each bead set is, in fact, a micro-system of its own. The final signal, as well as the background, is influenced by many factors including: the efficiency of the coupling reaction that links the capture oligonucleotides onto the bead sets; the efficiency of target amplification in the multiplexed TemPCR reaction; and the efficiency of hybridization during detection. As a result, the cutoff value for each pathogen (represented by each bead set) must be decided individually. The background signals (determined by averaging the values obtained from the RT-PCR blank and the samples that were known not to contain the target agent) were determined and the standard deviation obtained. The standard deviation was multiplied by five (5) and this value added to the average background. Values higher than the average background are considered positive results, indicating the presence of a particular agent.

Samples 24 were adenoviruses subtype 4, 7, and 21, respectively. Samples 5-11 were *Chlamydia pneumoniae* (CPN), *Mycoplasma pneumoniae* (MPN), Influenza A (INFA), Influenza B (INFB), Parainfluenza type 1 (PIV-1), Parainfluenza type 3 (PIV-3), and Respiratory syncytial virus (RSV), respectively. Sample 12 was SARS-CoV. To increase detection sensitivity and minimize false negative detection caused by target mutations, we selected three different target sequences from the SARS-CoV genome for amplification and detection. Samples 13-16 were different enteroviruses, including Coxsackie virus A (CVA), Coxsackie virus B (CVB), Rhinovirus (RhV), and Echovirus (EV). For detection of adenovirus and enterovirus species, each of the specific detection nucleotides for adenovirus and enterovirus species were added in the detection step.

As can be seen in Table 6, the TemPCR method of the present disclosure provided specific amplification of the target sequences, which were specifically detected by the corresponding detection oligonucleotides. The high detection specificity was evident by the high signal to background ratios obtained from each bead set. This result indicates the target enrichment primers amplified the correct target nucleic acid sequence in the presence of multiple primer sets not specific for the target sequence and that the target amplification primers (FSP and RSP) function correctly to amplify the target sequence as described and the appropriate detection oligonucleotides are capable of hybridizing to the target sequence being-detected.

EXAMPLE 3

In Examples 1 and 2 above, only 1 nucleic acid sample was added to each reaction (albeit in the presence of target enrichment primers specific for multiple agents). Table 7 shows the specificity of the TemPCR amplification method when nucleic acid samples from multiple pathogens were included in a single sample for multiplex amplification and subsequent detection. In this example, target enrichment primers for each organisms listed in Table 3 were included in each sample, along with the target amplification primers and nucleic acid from the indicated pathogens. The rows in Table 7 indicate the detection oligonucleotide detected during the multiplex detection step (note that detection oligonucleotides specific for the target sequences for all the organisms listed in Table 3 were included in each detection reaction) while the rows in Table 6 indicated the identity of the pathogen nucleic acid added to each sample. TemPCR amplification conditions and multiplex detection were carried out as described in Example 2 above.

Sample 1 is a negative control where no template nucleic acid was included in the RT-PCR reaction. Sample 2 included three pathogens, SARS, CPN, and INFA; Sample 3 included ADV-7, RSVB, and INFB; Sample 4 included PIV-3, CPN, and INFA; Sample 5 included ADV-21, RSVB, and INFB; Sample 6 included RhV and PIV1; Sample 7 included SARS and INFB; and Sample 8 included ADV-7 and PIV1. The cutoff values shown in Table 6 were used in this Example and values higher than the cutoff were highlighted in Table 7.

The results show that TemPCR correctly amplified the correct target sequence from each agent and that the amplified target sequences could be detected to provide an accurate and specific readout of the agents present in the sample. As one example, in row 2 nucleic acid from SARS, CPN and INFA was added to the amplification reaction. In the presence of the target enrichment primers specific for all the agents in Table 3, the TemPCR method using the primers disclosed correctly amplified the correct target sequences. No modification or optimization of the TemPCR amplification conditions was required to obtain correct multiplex amplification of the three agents. Importantly, the same set of TemPCR multiplex amplification conditions allowed the specific detection of a variety or of agents using a standardized amplification protocol. The TemPCR method described is highly specific and can detect specific pathogens in various combinations. No false positives or false negatives were observed.

EXAMPLE 4

To validate the sensitivity of the TemPCR method, 1 ml serum samples were prepared with different amounts of viral or bacterial agents as listed in Table 8. For each agent, four concentrations were prepared: $10^4$ pfu/ml, $10^3$ pfu/ml, $10^2$ pfu/ml, and $10^1$ pfu/ml. To observe the assay repeatability, at each of the four concentrations, triplicate samples were prepared and analyzed. Certain samples, such as ADV4 and RhV, did not have high titer stocks available and the starting concentration was $10^3$ pfu/ml. For SARS, the viral stock was limited, and therefore, only two samples were studied for each concentration (rather than three). A positive control sample at high concentration (not spiked into serum) was also included for each pathogen.

For each 1 ml of the spiked sample serum, 200 μl was used for nucleic acids isolation. Nucleic acid isolation was performed using the triazol method as described herein. At the end of the isolation procedure, the nucleic was eluted into 50 μl RNAse free water. A volume of 5 μl from this elution was used as template in a subsequent TemPCR reaction. Therefore, if the starting concentration was $10^4$ pfu/ml, the TemPCR amplification reaction included only about 200 copies of pathogen genomes. Similarly, at $10^3$ pfu/ml level, only 20 copies were included in the reaction system and so on. Conditions for the TemPCR amplification reaction were as described above in Example 2 and multiplex detection carried out as described in Example 2 using the direct detection method.

Table 8 shows the results of the sensitivity study. A cutoff value was determined for each target specifically and the cutoff values were set to be the mean plus 5 times of the standard deviation. Values above the cutoff were considered positive and were highlighted in the Table 8. In general, the assay could detect between 20-200 copies of pathogens present in a serum sample. It should be noted that TemPCR conditions used in this Example did not incorporate the selective amplification step discussed herein. The use of the selective amplification step is expected to increase the sensitivity of the reaction significantly.

EXAMPLE 5

Example 5 illustrates the results of an experiment utilizing an alternate embodiment of the TemPCR method. In this example, nucleic acid sequences from each disease agent and the secondary disease agents were obtained and isolated as described herein. The nucleic acid from each agent was amplified by the Tem-PCR method. In this embodiment, the amplification reaction conditions for TemPCR were altered to include a target enrichment step and a selective amplification step. The nucleic acid for each agent was placed in a separate reaction tube and the complete mix of primers specified in Table 3 was added along with reagents for RT-PCR. The primer rations used in this example were 1:1:1:1:10:40 ($F_{out}$:$F_{in}$:$R_{in}$:$R_{out}$:FSP:RSP).

The amplification conditions are given below. The reaction tubes were placed in a thermocycler programmed as follows: (i) reverse transcription—30 minutes at 50° C.; (ii) initial PCR activation—15 minutes at 95° C.; (iii) first amplification reaction comprising a first 3-step cycling (target enrichment)—0.5 minutes at 94° C., 1 minute at 52° C. and 1 minute at 72° C. for 15 complete cycles, and a second 2-step cycling (selective amplification)—15 seconds at 94° C., 1.5 minutes at 70° C.; for 6 complete cycles, preferably 4-8 complete cycles; (iv) second amplification reaction comprising a third 3-step cycling (target amplification)—15 to 30 seconds at 94° C., 15 to 30 seconds at 50-55° C. and 15 to 30 second at 72° C.; for at least 2 complete cycles, preferably for 10-40 complete cycles; and (v) final extension-3 minutes at 72° C. The detection of the amplified products containing the target sequence was carried out as described for the direct detection methodology using beads (obtained from Luminex Corporation, Austin, Tex.) as described in Example 1 and illustrated in FIG. 2. Detection oligonucleotides for each agent listed in Table 3 were added to each detection reaction.

TABLE 1

Exemplary ratios of nested primers and super primers for disease agents and secondary disease agents with the indicated genomes. The ratios of nested primers and super primers may be varied as discussed in the instant specification.

|  | DNA | RNA (+) | RNA (−) |
|---|---|---|---|
| $F_{out}$ | 1 | 1 | 4 |
| $R_{out}$ | 1 | 4 | 1 |
| $F_{in}$ | 1 | 1 | 1 |
| $R_{in}$ | 1 | 1 | 1 |
| FSP | 8 | 8 | 8 |
| RSP | 32 | 32 | 32 |

TABLE 5

Description of the included pathogen targets and detectable strains.

| No. | Pathogen | Name in Product | Tageted gene | Detectable types/strains |
|---|---|---|---|---|
| 1 | SARS-CoV | SARS1 | 5'end polyprotein | |
| | | SARS2 | Polymerase gene | |
| | | SARS3 | N gene | |
| 2 | Influenza A | INFA | NS gene | H1N1, H1N2, H2N2, H3N2, H3N8, H4N6, H4N8, H5N1, H5N2, H5N3, H6N1, H6N2, H6N4, H7N1, H7N2, H7N3, H7N7, H7N8, H9N2, H10N5, H11N1 H11N8 H11N9 |
| 3 | Influenza B | INFB | NS gene | |
| 4 | Adenoviruses | ADV | Hexon gene | Type 3, 4, 7, 14, and 21. |
| 5 | Parainfluenza1 | PIV1 | N gene | |
| 6 | Parainfluenza3 | PIV3 | N gene | |
| 7 | Respiratory syncytial virus | RSV | NS gene | RSVA and RSVB |
| 8 | *M. pneumoniae* | MPN | cytadhesin P1 gene | |
| 9 | *C. pneumoniae* | CPN | Uridine Kinase gene | |
| 10 | Enteroviruses | ENT | 5'UTR | Rhinovirls 1a, 1b, 2, 9, 14, 15, 16, 39, 49, 50, 85, 89; Coxackie Virus A: A21, A24; Coxsackie Virus B: B4, B5: Echoviru:s 11, 20, and 25. |

TABLE 2

Primer sequences and detection oligonucleotide sequences used in the multiplex amplification in one embodiment of the method disclosed.

| GenBank ID | Target Name | Oligonucleotides sequences | Positions |
|---|---|---|---|
| AY278491 | SARS | | |
| | SARS1Fo | ACCGTAGACTCATCTCTATGATG | 18121-18143 |
| | SARS1Fi | CAGGCCACGTTTTGTCATGCGAAGCTATTCGTCACGTTCG | 18201-18220 |
| | SARS1Ro | TTGCATTAACTCTGGTGAATTCTG | 18384-18361 |
| | SARS1Ri | TTCTTTGCGTTATGTCTCTGCTGTAGAAAATCCTAGCTGG | 18309-18290 |
| | SARS1De | TAGAGGGCTGTCATGCAACT | 18241-18260 |
| | SARS2Fo | ATGCCTAACATGCTTAGGATAATG | 15246-15269 |
| | SARS2Fi | CAGGCCACGTTTTGTCATGCTTTCTACAGGTTAGCTAACGA | 15323-15343 |
| | SARS2Ro | TACATTGGCTGTAACAGCTTGAC | 15482-15460 |
| | SARS2Ri | TTCTTTGCGTTATGTCTCTGAGCATAAGCAGTTGTAGCATC | 15440-15420 |
| | SARS2De | GTGAGATGGTCATGTGTGGC | 15361-15380 |
| | SARS3Fo | ACAATGCTGCCACCGTGCTAC | 28580-28600 |
| | SARS3Fi | CAGGCCACGTTTTGTCATGCCCTCAAGGAACAACATTGCC | 28606-28625 |
| | SARS3Ro | TAGCGCGAGGGCAGTTTCAC | 28785-28766 |
| | SARS3Ri | TTCTTTGCGTTATGTCTCTGCCGCTAGCCATTCGAGCAGG | 28760-28741 |
| | SARS3De | ATCATCACGTAGTCGCGGTAA | 28681-18700 |
| M11486 | RSVA | | |
| | RSVAFo | ATTGGCATTAAGCCTACAAA | 899-918 |
| | RSVAFi | CAGGCCACGTTTTGTCATGCGGGCAAATACAAAGATGGCTC | 1082-1102 |
| | RSVARo | GACATAGCATATAACATACCTATT | 1310-1287 |
| | RSVARi | TTCTTTGCGTTATGTCTCTGGGAGTRTCAATAYTATCCCTGT | 1202-1180 |
| | RSVADe | CACTCAACAAAGATCAACTT | 1127-1146 |
| D00736 | RSVB | | |
| | RSVBFo | ATTGGCATTAAGCCTACAAA | 888-907 |
| | RSVBFi | CAGGCCACGTTTTGTCATGCGGGCAAATACAAAGATGGCTC | 1071-1091 |
| | RSVBRo | GACATAGCATATAACATACCTATT | 1299-1276 |
| | RSVBRi | TTCTTTGCGTTATGTCTCTGGGAGTRTCAATAYTATCCCTGT | 1191-1169 |
| | RSVBDe | CATTAAATAAGGATCAGCTG | 1116-1135 |
| AF457102 | PIV-1 | | |
| | PIV1Fo | CACAATTGATATGAATTATTGG | 13037-13058 |
| | PIV1Fi | CAGGCCACGTTTTGTCATGCTGATGAAATAATTAGAGCAACTAG | 13064-13087 |
| | PIV1Ro | CTATTWATATCATCATCATTT | 13186-13166 |
| | PIV1Ri | TTCTTTGCGTTATGTCTCTGTGCTATCATTTCTTTAAGATTG | 13160-13139 |
| | PIV1De | CAGCTATGACTATTGCAGAC | 13096-13115 |

TABLE 2-continued

Primer sequences and detection oligonucleotide sequences used in the multiplex amplification in one embodiment of the method disclosed.

| GenBank ID | Target Name | | Oligonucleotides sequences | Positions |
|---|---|---|---|---|
| Z11575 | PIV-3 | | | |
| | | PIV3Fo | CACAATTGATATGAATTATTGG | 12911-12932 |
| | | PIV3Fi | CAGGCCACGTTTTGTCATGCTACTGACATCATACATGCAATTTC | 12938-12961 |
| | | PIV3Ro | CTATTWATATCATCATCATTT | 13060-13040 |
| | | PIV3Ri | TTCTTTGCGTTATGTCTCTGTAACTATTATCTCTTTTAAATT | 13035-13014 |
| | | PIV3De | CTGCAATTACAATAGCAGAT | 12970-12989 |
| NC_000912 | M. Pneumoniae | | | |
| | | MPMFo | ACCAGCATAAGAACCTCCTG | 323867-323886 |
| | | MPMFi | CAGGCCACGTTTTGTCATGCTCAAGTCACGTACTCGCCATC | 323891-232911 |
| | | MPMRo | TTAAACTGTTACTGTTGTGC | 324086-324067 |
| | | MPMRi | TTCTTTGCGTTATGTCTCTGTTTGCGAGATCTCGAGGGGTC | 324039-324019 |
| | | MPMDe | GCTGAATAAACCGGGTATTA | 323961-323980 |
| AE001618 | C. Pneumoniae | | | |
| | | CPMFo | GCCTGCCCTATGAAAACGATG | 6780-6800 |
| | | CPMFi | CAGGCCACGTTTTGTCATGCCGTGATCCACACGAGTCATAC | 6850-6870 |
| | | CPMRo | TAAAGCTGCTTCGGGAACGTG | 6970-6950 |
| | | CPMRi | TTCTTTGCGTTATGTCTCTGTATCGGGGTTGTATTTCCTTC | 6943-6923 |
| | | CPMDe | ATCGGAAGTCGCTCTATCTT | 6885-6904 |
| AY027864 | Enterovirus | | | |
| | | ENTVFo | CCTCCCGCCCCTGAATGCGG | 1-20 |
| | | ENTVFi | CAGGCCACGTTTTGTCATGCCCTAACTGTGGAGCACATGCC | 26-46 |
| | | ENTVRo | TGTCACCATAAGCAGCCAATG | 152-132 |
| | | ENTVRi | TTCTTTGCGTTATGTCTCTGTAGTCGGTTCCGCTGCAGAG | 100-81 |
| | | ENTVDe | CCAGAGGGTAGTGTGTCGTA | 53-72 |
| AJ344037 | InfluenzaA | | | |
| | | INFAFo | TGCAATTGGGGTCCTCATCGG | 528-548 |
| | | INFAFi | CAGGCCACGTTTTGTCATGCTTGAATGGAATGATAACACAG | 554-574 |
| | | INFARo | AAACGAGAAAGTTCTTATCTC | 826-806 |
| | | INFARi | TTCTTTGCGTTATGTCTCTGGTTCTCGCCATTTTCCGTTTC | 674-654 |
| | | INFADe | TCTACAGAGATTCGCTTGG | 591-609 |
| AF492482 | InfluenzaB | | | |
| | | INFBFo | TGAAGGGTTTGAGCCATACTG | 291-311 |
| | | INFBFi | CAGGCCACGTTTTGTCATGCTACAATTGGACCGATTACCCT | 346-366 |
| | | INFBRo | TGAGTGTTTACTTCCTCCTTTATC | 497-474 |
| | | INFBRi | TTCTTTGCGTTATGTCTCTGGTTGTTCATGTCCCTTAATACT | 456-435 |
| | | INFBDe | CCTTGATGACATAGAAGAAG | 384-403 |
| AF542122 | Adenovirus | | | |
| | | ADVFo | AACAGACCCAAYTACATTGG | 910-929 |
| | | ADVFi | CAGGCCACGTTTTGTCATGCATGTACTACAACAGTACTGG | 955-974 |
| | | ADVRo | TATGACAGTTCWGTGTTTCTGTC | 1052-1033 |
| | | ADVRi | TTCTTGCGTTATGTCTCTGGCAAGTCAACCACHGCATTC | 1030-1011 |
| AY008279 | ADV21De | | GAGTGCTGGCAGGTCAAGCA | 1034-1053 |
| AF542129 | ADV3De | | GAGTTTTGGCTGGCCAAGCA | 1016-1035 |
| AF542122 | ADV4De | | GGGTACTGGCCGGTCAGGCC | 983-1002 |
| AF515814 | ADV7De | | GAGTTTTGGCCGGCCAAGCA | 1131-1150 |
| AB018425 | ADV14De | | GGGTGCTGGCTGGCCAAGCA | 717-736 |

Super primer sequences
FSP-CAGGCCACGTTTTGTCATGC

RSP-TTCTTTGCGTTATGTCTCTG

TABLE 3

Primer sequences and detection oligonucleotide sequences used in the multiplex amplification in one embodiment of the method disclosed.

Sequence 5' to 3'

SARS

| | |
|---|---|
| SARS1Fo | ACCGTAGACTCATCTCTATGATG |
| SARS1Fi | CAGGCCACGTTTTGTCATGCGAAGCTATTCGTCACGTTCG |
| SARS1Ro | TTGCATTAACTCTGGTGAATTCTG |
| SARS1Ri | TTCTTTGCGTTATGTCTCTGCTGTAGAAAATCCTAGCTGG |
| SARS2Fo | ATGCCTAACATGCTTAGGATAATG |
| SARS2Fi | CAGGCCACGTTTTGTCATGCTTTCTACAGGTTAGCTAACGA |
| SARS2Ro | TACATTGGCTGTAACAGCTTGAG |
| SARS2Ri | TTCTTTGCGTTATGTCTCTGAGCATAAGCAGTTGTAGCATC |
| SARS4Fo | ACAATGCTGCGACGGTGCTAC |
| SARS4Fi | CAGGCCACGTTTTGTCATGCCCTCAAGGAACAACATTGCC |
| SARS4Ro | TAGCGCGAGGGCAGTTTCAC |
| SARS4Ri | TTCTTTGCGTTATGTCTCTGCCGCTAGCCATTCGAGCAGG |
| SARS1De | TAGAGGGCTGTCATGCAAGT |
| SARS2De | GTGAGATGGTCATGTGTGGC |
| SARS4De | TCATCACGTAGTCGGGGTAA |

RSV A

| | |
|---|---|
| RSVAFo | AAGAATTTGATAAGTACCAC |
| RSVAFi | CAGGCCACGTTTTGTCATGCACTCCCTTGGTTAGAGATGG |
| RSVARi | TTCTTTGCGTTATGTCTCTGCAATGCTACTTCATCATTGTC |
| RSVARo | TATGTATCACTGCCTTAGCC |
| RSVADe | GCAGGAATTCATTGAGTATG |

RSV B

| | |
|---|---|
| RSVBFo | AATAAGAATTTGATAAGTGC |
| RSVBFi | CAGGCCACGTTTTGTCATGCACCTTTTCAATCAGAAATGG |
| RSVBRi | TTCTTTGCGTTATGTCTCTGCAATGCTACTTCGTCATTGTC |
| RSVBRo | TGCTTTGCTAATGCATTGG |
| RSVBDe | GGTGCAATTCACTGAGCATG |

PIV1

| | |
|---|---|
| PIV1Fo | AGTATCACTCCTTGCAATGG |
| PIV1Fi | CAGGCCACGTTTTGTCATGCATCTCACTACAAACGGTGTC |
| PIV1Ri | TTCTTTGCGTTATGTCTCTGTTTGACAATGAACCCATCTG |
| PIV1Ro | GTTCTTTCATACTCCATGTC |
| PIV1De | GCTGATGTCAAGTATGTGAT |

PIV3

| | |
|---|---|
| PIV3Fo | TCAATGGCTTATGCCAATCC |
| PIV3Fi | CAGGCCACGTTTTGTCATGCACAACAAATGGAAGTAATGC |
| PIV3RI | TTCTTTGCGTTATGTCTCTGCTCGTCTTAACCACAAATCC |
| PIV3Ro | CAGGTCACTTCCAAATATCC |
| PIV3De | CTAAAACGGCAAAAGTATGG |

InfA

| | |
|---|---|
| INFAFo | TGCAATTGGGGTCCTCATCGG |
| INFAFi | CAGGCCACGTTTTGTCATGCTTGAATGGAATGATAACACAG |
| INFARo | AAACGAGAAAGTTCTTATCTC |
| INFARi | TTCTTTGCGTTATGTCTCTGGTTCTCGCCATTTTCCGTTTC |
| INFADeC | TCTACAGAGATTCGCTTGG |

INFB

| | |
|---|---|
| INFBFo | AGTCTTATCCCAATTTGGTC |
| INFBFi | CAGGCCACGTTTTGTCATGCAGAGCACCGATTATCACCAG |
| INFBRi | TTCTTTGCGTTATGTCTCTGCATGTCAGCTATTATGGAGC |
| INFBRo | AAGCACTGCCTGCTGTACAC |
| INFBDe | TTCCACAAAACAGTAATAGC |

MPN

| | |
|---|---|
| MPNFo | ATCACCTTTAACCCCTTTGG |
| MPNFi | CAGGCCACGTTTTGTCATGCCGGCTTTGGTTTGAGTGGG |
| MPNRi | TTCTTTGCGTTATGTCTCTGCGCGGCACGAGTAAAACGGC |
| MPNRo | TGCAACTGCTCATAGTACAC |
| MPNDe | TGCACCCCAAGAGTGAAACG |

CPN

| | |
|---|---|
| CPN 5 Fo | GAAATTTATAGAGCGGACTCG |
| CPN 5 Fi | CAGGCCACGTTTTGTCATGCGCTGATATCATTGTACATGG |
| CPN 5 Ro | GTTGACCATATAATACGTCTC |
| CPN 5 Ri | TTCTTTGCGTTATGTCTCTGGCTTTCCAGGGCATTCTC |
| CPN5 De | ACCGACAAAACGTAGTAACA |

ENTV

| | |
|---|---|
| CVA2 Fo | CAAGGTGTGAAGAGCCTATTG |
| CVBEV Fo | CATGGTGCGAAGAGTCTATTG |
| RhV2 Fo | GTGAAGAGC(GC)CGTGTGCTC |
| ENT3 Fi | TTCTTTGCGTTATGTCTCTGAGTCCTCCGGCCCCTGAATG |
| ENT3 Ri | CAGGCCACGTTTTGTCATGCAAACACGGACACCCAAAGTAG |
| CVEV Ro | ATTGTCACCATAAGGAGCC |
| RhV2 Ro | TATATATTGTCACCATAAGC |
| CVEV De | GTTAGGATTAGCCGCATTCA |
| RhV2 De | GTTGGTCCCATCCCGGAATT |

ADV

| | |
|---|---|
| ADV3-3Fi | CAGGCCACGTTTTGTCATGCCCCATGGATGAGCCCACCC |
| ADV3-3Ri | TTCTTTGCGTTATGTCTCTGGCTGGTGCACTCTGACCACG |
| ADV4-3Ri | TTCTTTGCGTTATGTCTCTGGCTGGTGCACTCGGACGACG |
| ADV14-3Ri | TTCTTTGCGTTATGTCTCTGGCTGATGCACTCTGACCACG |
| ADV3-3Fo | AGCAACTTCATGTCYATGGG |
| ADV3-3Ro | GTGCGCAGGTAGAGGGCCTC |
| ADV14-3Ro | GTACGCAGGTAGACTGTCTC |
| ADV3-3De | GCTTTATCTTCTTTTCGAAG |
| ADV4-3De | TCTCTATGTTGTCTTCGAAG |
| ADV14-3De | GCTTTATCTTCTCTTCGAAG |

Super-primers

| | |
|---|---|
| FSP | CAGGCCACGTTTTGTCATGC |
| RSP | TTCTTTGCGTTATGTCTCTG |

TABLE 4

| | Sample | RSVB | SARS1 | SARS2 | SARS3 | PIV-1 | MPN | CPN | ENT | INFA | INFB | ADV3 | ADV7 | ADV14 | ADV21 |
|---|---|---|---|---|---|---|---|---|---|---|---|---|---|---|---|
| 1 | LUM Blank | 20 | 12 | 16 | 24 | 21 | 16 | 19 | 17 | 20 | 22 | 25 | 25 | 25 | 32 |
| 2 | Blank 4:1:1:1:8:16 | 16 | 7 | 8 | 13 | 15 | 16 | 12 | 16 | 12 | 19 | 10 | 13 | 11 | 14 |
| 3 | Blank 4:1:1:1:8:24 | 16 | 25 | 10 | 10 | 15 | 15 | 16 | 12 | 22 | 14 | 16 | 15 | 14 | 18 |
| 4 | Blank 4:1:1:1:8:32 | 16 | 26 | 21 | 13 | 4 | 10 | 13 | 24 | 16 | 18 | 14 | 17 | 14 | 24 |
| 5 | RSVB 4:1:1:1:8:16 | 1102 | 14 | 20 | 13 | 14 | 7 | 10 | 16 | 14 | 17 | 13 | 17 | 17 | 19 |
| 6 | RSVB 4:1:1:1:8:24 | 1377 | 12 | 8 | 10 | 14 | 7 | 14 | 12 | 19 | 24 | 17 | 11 | 11 | 28 |
| 7 | RSVB 4:1:1:1:8:32 | 1496 | 26 | 10 | 10 | 11 | 13 | 10 | 13 | 15 | 14 | 9 | 12 | 16 | 19 |
| 8 | PIV1 4:1:1:1:8:16 | 19 | 22 | 10 | 11 | 311 | 18 | 12 | 19 | 10 | 15 | 10 | 18 | 26 | 18 |

TABLE 4-continued

| Sample | RSVB | SARS1 | SARS2 | SARS3 | PIV-1 | MPN | CPN | ENT | INFA | INFB | ADV3 | ADV7 | ADV14 | ADV21 |
|---|---|---|---|---|---|---|---|---|---|---|---|---|---|---|
| 9 PIV1 4:1:1:1:8:24 | 9 | 19 | 15 | 12 | 298 | 12 | 18 | 19 | 13 | 12 | 13 | 13 | 12 | 20 |
| 10 PIV1 4:1:1:1:8:32 | 13 | 38 | 17 | 9 | 514 | 20 | 22 | 29 | 15 | 23 | 11 | 13 | 16 | 16 |
| 11 INFA 4:1:1:1:8:16 | 10 | 31 | 15 | 17 | 8 | 13 | 14 | 119 | 260 | 19 | 18 | 11 | 22 | 30 |
| 12 INFA 4:1:1:1:8:24 | 26 | 46 | 23 | 8 | 9 | 10 | 13 | 186 | 454 | 15 | 9 | 9 | 15 | 23 |
| 13 INFA 4:1:1:1:8:32 | 21 | 91 | 28 | 17 | 7 | 10 | 16 | 323 | 630 | 42 | 10 | 16 | 22 | 29 |
| 14 INFB 4:1:1:1:8:16 | 10 | 22 | 18 | 27 | 14 | 9 | 6 | 13 | 16 | 677 | 12 | 21 | 16 | 23 |
| 15 INFB 4:1:1:1:8:24 | 6 | 14 | 12 | 37 | 6 | 11 | 7 | 16 | 14 | 1162 | 10 | 15 | 12 | 23 |
| 16 INFB 4:1:1:1:8:32 | 5 | 29 | 21 | 51 | 11 | 9 | 13 | 23 | 12 | 1480 | 11 | 14 | 13 | 20 |
| 17 ADV21 4:1:1:1:8:16 | 8 | 10 | 19 | 9 | 13 | 19 | 13 | 21 | 13 | 17 | 11 | 13 | 12 | 286 |
| 18 ADV21 4:1:1:1:8:24 | 9 | 18 | 12 | 8 | 12 | 10 | 15 | 21 | 13 | 17 | 13 | 15 | 14 | 452 |
| 19 ADV21 4:1:1:1:8:32 | 12 | 43 | 17 | 8 | 11 | 6 | 11 | 25 | 13 | 19 | 11 | 10 | 10 | 543 |
| 20 MPN 4:1:1:1:8:16 | 16 | 16 | 8 | 19 | 4 | 330 | 16 | 16 | 20 | 16 | 19 | 17 | 13 | 25 |
| 21 MPN 4:1:1:1:8:24 | 15 | 29 | 27 | 15 | 3 | 1182 | 21 | 19 | 21 | 17 | 18 | 20 | 16 | 23 |
| 22 MPN 4:1:1:1:8:32 | 10 | 30 | 21 | 16 | 14 | 1317 | 12 | 27 | 13 | 25 | 15 | 19 | 20 | 23 |
| 23 CPN 4:1:1:1:8:16 | 14 | 22 | 12 | 12 | 7 | 19 | 1109 | 19 | 17 | 25 | 13 | 13 | 13 | 19 |
| 24 CPN 4:1:1:1:8:24 | 23 | 27 | 15 | 12 | 7 | 10 | 1342 | 18 | 16 | 21 | 19 | 13 | 17 | 23 |
| 25 CPN 4:1:1:1:8:32 | 13 | 43 | 30 | 13 | 8 | 20 | 1828 | 18 | 13 | 30 | 11 | 15 | 17 | 17 |
| 26 SARS 4:1:1:1:8:16 | 11 | 857 | 768 | 227 | 12 | 17 | 11 | 14 | 20 | 20 | 14 | 17 | 21 | 20 |
| 27 SARS 4:1:1:1:8:24 | 11 | 1251 | 1097 | 376 | 15 | 17 | 11 | 18 | 17 | 17 | 15 | 19 | 15 | 24 |
| 28 SARS 4:1:1:1:8:32 | 7 | 1638 | 1528 | 693 | 9 | 13 | 6 | 20 | 16 | 19 | 14 | 13 | 14 | 17 |

RSV = respiratory syncytial virus; PIV = parainfluenza virus; INF = influenza virus; ADV + adenovirus; MPN = Mycoplasma pneumonia; CPN = Chlamydia pneumonia; SARS = severe acute respiratory syndrome virus

TABLE 6

| Sample/Target | ADV | CPN | MPN | INFA | INFB | PIV1 | PIV3 | RSV | SARS1 | SARS2 | SARS4 | ENT |
|---|---|---|---|---|---|---|---|---|---|---|---|---|
| 1 RT-PCR Blank | 13 | 8 | 12 | 15 | 10 | 10 | 27 | 4 | 6 | 10 | 8 | 9 |
| 2 ADV-4 | 1134 | 17 | 7 | 20 | 7 | 11 | 20 | 5 | 4 | 6 | 4 | 4 |
| 3 ADV-7 | 530 | 8 | 10 | 8 | 7 | 10 | 23 | 8 | 3 | 10 | 4 | 13 |
| 4 ADV-21 | 968 | 17 | 7 | 14 | 13 | 15 | 29 | 6 | 9 | 11 | 9 | 14 |
| 5 CPN | 21 | 661 | 13 | 19 | 24 | 27 | 66 | 6 | 5 | 9 | 12 | 14 |
| 6 MPN | 11 | 33 | 1696 | 25 | 21 | 21 | 77 | 17 | 16 | 7 | 12 | 12 |
| 7 INFA | 25 | 32 | 16 | 809 | 73 | 22 | 105 | 17 | 10 | 8 | 13 | 12 |
| 8 INFB | 19 | 41 | 10 | 21 | 2061 | 27 | 89 | 12 | 10 | 11 | 18 | 13 |
| 9 PIV-1 | 24 | 30 | 9 | 12 | 24 | 1705 | 65 | 11 | 10 | 10 | 12 | 13 |
| 10 PIV-3 | 26 | 41 | 14 | 25 | 35 | 40 | 1802 | 19 | 12 | 15 | 14 | 20 |
| 11 RSV | 17 | 34 | 9 | 21 | 18 | 23 | 76 | 1782 | 12 | 22 | 13 | 8 |
| 12 SARS | 26 | 36 | 16 | 27 | 37 | 21 | 74 | 16 | 2374 | 1934 | 437 | 1 |
| 13 CVA | 15 | 43 | 17 | 25 | 31 | 27 | 80 | 17 | 19 | 10 | 17 | 2833 |
| 14 CVB | 58 | 39 | 17 | 30 | 38 | 28 | 85 | 15 | 14 | 16 | 18 | 3254 |
| 15 RhV | 12 | 19 | 7 | 20 | 8 | 13 | 34 | 12 | 9 | 2 | 8 | 1329 |
| 16 EV | 6 | 14 | 14 | 17 | 9 | 12 | 31 | 8 | 24 | 10 | 6 | 159 |
| Average Bkg | 21.0 | 27.4 | 11.7 | 19.7 | 23.6 | 20.4 | 58.6 | 11.4 | 10.7 | 10.4 | 11.1 | 10.9 |
| Standard deviation | 12.8 | 12.3 | 3.8 | 6.0 | 17.6 | 8.6 | 28.4 | 5.2 | 4.7 | 4.5 | 4.6 | 4.9 |
| Cutoff | 85.1 | 88.8 | 30.6 | 49.7 | 111.7 | 63.4 | 200.4 | 37.2 | 39.5 | 33.8 | 34.0 | 35.5 |
| Signal/Background | 41.9 | 24.2 | 144.5 | 41.0 | 87.3 | 83.6 | 30.8 | 155.9 | 221.2 | 186.6 | 39.3 | 173.5 |

RSV = respiratory syncytial virus; PIV = parainfluenza virus; INF = influenza virus; ADV + adenovirus; MPN = Mycoplasma pneumonia; CPN = Chlamydia pneumonia, SARS = severe acute respiratory syndrome virus

TABLE 7

| Sample/Target | ADV | CPN | MPN | INFA | INFB | PIV1 | PIV3 | RSV | SARS1 | SARS2 | SARS4 | ENT |
|---|---|---|---|---|---|---|---|---|---|---|---|---|
| 1 RT-PCR Blank | 35 | 25 | 18 | 24 | 32 | 18 | 45 | 12 | 9 | 7 | 10 | 12 |
| 2 SARS/CPN/INFA | 8 | 93 | 10 | 630 | 36 | 13 | 70 | 10 | 746 | 823 | 104 | 11 |
| 3 ADV-7/RSVB/INFB | 303 | 23 | 8 | 29 | 1482 | 15 | 61 | 1823 | 11 | 13 | 12 | 11 |
| 4 PIV-3/CPN/INFA | 16 | 152 | 8 | 664 | 41 | 17 | 1156 | 13 | 7 | 11 | 9 | 9 |
| 5 ADV-21/RSVB/INFB | 983 | 23 | 10 | 28 | 1665 | 19 | 53 | 1845 | 11 | 9 | 3 | 11 |
| 6 RhV/PIV-1 | 26 | 21 | 7 | 31 | 32 | 1712 | 51 | 14 | 6 | 7 | 11 | 958 |
| 7 SARS/INFB | 18 | 15 | 9 | 19 | 1458 | 20 | 41 | 10 | 1799 | 1560 | 316 | 15 |
| 8 ADV-7/PIV-1 | 593 | 18 | 12 | 22 | 27 | 1611 | 49 | 15 | 13 | 16 | 14 | 16 |
| Cutoff values | 85.1 | 88.8 | 30.6 | 49.7 | 111.7 | 63.4 | 200.4 | 37.2 | 39.5 | 33.8 | 34.0 | 35.5 |

RSV = respiratory syncytial virus; PIV = parainflueriza virus; INF = influenza virus; ADV + adenovirus; MPN = Mycoplasma pneumonia; CPN = Chlamydia pneumonia; SARS = severe acute respiratory syndrome virus

TABLE 8

Table 4 The sensitivity of the assay system

| | Sample/Target | ADV | CPN | MPN | INFA | INFB | PIV1 | PIV3 | RSV | SARS1 | SARS2 | SARS3 | ENT |
|---|---|---|---|---|---|---|---|---|---|---|---|---|---|
| 1 | RT-PCR Blank | 8 | 35 | 7 | 21 | 37 | 16 | 85 | 16 | 11 | 5 | 14 | 9 |
| 2 | Serum only | 12 | 40 | 11 | 29 | 37 | 10 | 71 | 9 | 8 | 6 | 9 | 9 |
| 3 | Serum only | 13 | 32 | 7 | 24 | 34 | 13 | 76 | 9 | 6 | 4 | 11 | 7 |
| 4 | Serum only | 11 | 31 | 6 | 27 | 28 | 19 | 85 | 8 | 10 | 5 | 11 | 10 |
| 5 | ADV4 10e3 ctrl | 976 | 38 | 15 | 32 | 22 | 20 | 76 | 6 | 8 | 9 | 19 | 18 |
| 6 | ADV4 10e3 #1 | 466 | 45 | 12 | 36 | 30 | 18 | 82 | 10 | 9 | 14 | 15 | 24 |
| 7 | ADV4 10e3 #2 | 112 | 42 | 6 | 31 | 34 | 25 | 93 | 13 | 23 | 20 | 16 | 19 |
| 8 | ADV4 10e3 #3 | 105 | 40 | 20 | 27 | 20 | 26 | 81 | 16 | 9 | 10 | 6 | 17 |
| 9 | ADV4 10e2 #1 | 122 | 41 | 20 | 35 | 38 | 27 | 91 | 18 | 14 | 13 | 16 | 23 |
| 10 | ADV4 10e2 #2 | 162 | 42 | 16 | 28 | 28 | 27 | 54 | 23 | 10 | 15 | 16 | 18 |
| 11 | ADV4 10e2 #3 | 35 | 42 | 12 | 33 | 23 | 22 | 67 | 8 | 15 | 10 | 7 | 2 |
| 12 | ADV4 10e1 #1 | 31 | 39 | 15 | 32 | 29 | 26 | 82 | 8 | 15 | 16 | 13 | 22 |
| 13 | ADV4 10e1 #2 | 25 | 33 | 23 | 38 | 16 | 26 | 63 | 20 | 18 | 13 | 24 | 14 |
| 14 | ADV4 10e1 #3 | 25 | 28 | 22 | 25 | 10 | 28 | 59 | 21 | 21 | 18 | 10 | 11 |
| 28 | CPN 10e4 ctrl | 23 | 362 | 17 | 34 | 24 | 30 | 66 | 18 | 11 | 14 | 16 | 45 |
| 29 | CPN 10e4 #1 | 10 | 256 | 12 | 33 | 24 | 26 | 73 | 18 | 14 | 35 | 33 | 9 |
| 30 | CPN 10e4 #2 | 18 | 111 | 9 | 34 | 27 | 24 | 38 | 7 | 13 | 13 | 22 | 13 |
| 31 | CPN 10e4 #3 | 16 | 239 | 8 | 24 | 19 | 21 | 25 | 17 | 19 | 9 | 13 | 32 |
| 32 | CPN 10e3 #1 | 16 | 103 | 13 | 31 | 26 | 26 | 88 | 11 | 17 | 8 | 9 | 18 |
| 33 | CPN 10e3 #2 | 14 | 43 | 12 | 41 | 23 | 23 | 91 | 14 | 10 | 12 | 13 | 9 |
| 34 | CPN 10e3 #3 | 15 | 85 | 12 | 35 | 15 | 27 | 79 | 14 | 10 | 17 | 17 | 7 |
| 35 | CPN 10e2 #1 | 11 | 33 | 9 | 28 | 19 | 18 | 56 | 15 | 10 | 6 | 7 | 19 |
| 36 | CPN 10e2 #2 | 6 | 35 | 8 | 34 | 23 | 26 | 53 | 13 | 11 | 10 | 6 | 12 |
| 37 | CPN 10e2 #3 | 19 | 42 | 11 | 24 | 22 | 20 | 63 | 9 | 12 | 10 | 11 | 19 |
| 38 | CPN 10e1 #1 | 11 | 42 | 10 | 31 | 13 | 17 | 65 | 4 | 10 | 7 | 13 | 17 |
| 39 | CPN 10e1 #2 | 22 | 32 | 17 | 25 | 20 | 24 | 47 | 14 | 15 | 13 | 13 | 4 |
| 40 | CPN 10e1 #3 | 13 | 32 | 13 | 29 | 17 | 25 | 41 | 12 | 8 | 8 | 13 | 17 |
| 41 | MPN 10e4 ctrl | 12 | 34 | 578 | 29 | 32 | 19 | 75 | 11 | 8 | 12 | 6 | 11 |
| 42 | MPN 104 #1 | 13 | 33 | 262 | 24 | 39 | 12 | 76 | 12 | 6 | 10 | 9 | 6 |
| 43 | MPN 104 #2 | 9 | 28 | 354 | 21 | 17 | 15 | 57 | 12 | 8 | 4 | 12 | 9 |
| 44 | MPN 104 #3 | 12 | 30 | 428 | 23 | 18 | 15 | 55 | 8 | 4 | 4 | 15 | 12 |
| 45 | MPN 103 #1 | 14 | 34 | 109 | 22 | 21 | 12 | 88 | 11 | 13 | 12 | 7 | 7 |
| 46 | MPN 103 #2 | 11 | 37 | 23 | 28 | 19 | 13 | 95 | 9 | 13 | 10 | 14 | 6 |
| 47 | MPN 103 #3 | 8 | 37 | 82 | 30 | 22 | 12 | 72 | 7 | 7 | 7 | 8 | 9 |
| 48 | MPN 102 #1 | 6 | 54 | 9 | 36 | 21 | 21 | 124 | 12 | 10 | 11 | 7 | 17 |
| 49 | MPN 102 #2 | 12 | 42 | 18 | 28 | 22 | 7 | 96 | 9 | 1 | 13 | 13 | 10 |
| 50 | MPN 102 #3 | 13 | 39 | 19 | 29 | 18 | 10 | 105 | 17 | 7 | 4 | 9 | 11 |
| 51 | MPN 101 #1 | 8 | 38 | 11 | 20 | 21 | 16 | 101 | 16 | 4 | 3 | 14 | 0 |
| 52 | MPN 101 #2 | 11 | 38 | 9 | 32 | 26 | 17 | 102 | 10 | 5 | 12 | 11 | 10 |
| 53 | MPN 101 #3 | 13 | 34 | 15 | 31 | 19 | 11 | 91 | 14 | 12 | 6 | 11 | 10 |
| 54 | INFA 10e4 ctrl | 16 | 35 | 16 | 840 | 36 | 14 | 92 | 15 | 16 | 12 | 13 | 11 |
| 55 | INFA 10e4 #1 | 20 | 38 | 18 | 322 | 38 | 21 | 83 | 17 | 9 | 7 | 9 | 13 |
| 56 | INFA 10e4 #2 | 17 | 33 | 14 | 339 | 43 | 15 | 92 | 14 | 13 | 11 | 10 | 17 |
| 57 | INFA 10e4 #3 | 11 | 45 | 19 | 478 | 42 | 23 | 101 | 8 | 11 | 14 | 17 | 21 |
| 58 | INFA 10e3 #1 | 14 | 46 | 10 | 103 | 20 | 15 | 67 | 16 | 5 | 8 | 15 | 8 |
| 59 | INFA 10e3 #2 | 20 | 41 | 11 | 113 | 26 | 11 | 83 | 18 | 9 | 15 | 6 | 13 |
| 60 | INFA 10e3 #3 | 11 | 45 | 11 | 206 | 25 | 14 | 76 | 17 | 7 | 13 | 11 | 17 |
| 61 | INFA 10e2 #1 | 12 | 26 | 7 | 49 | 15 | 17 | 47 | 12 | 5 | 8 | 11 | 21 |
| 62 | INFA 10e2 #2 | 14 | 21 | 6 | 97 | 24 | 22 | 47 | 16 | 13 | 5 | 18 | 16 |
| 63 | INFA 10e2 #3 | 15 | 32 | 7 | 90 | 18 | 18 | 38 | 20 | 4 | 6 | 15 | 12 |
| 64 | INFA 10e1 #1 | 12 | 27 | 14 | 36 | 3 | 19 | 48 | 14 | 12 | 16 | 6 | 13 |
| 65 | INFA 10e1 #2 | 16 | 26 | 12 | 31 | 14 | 30 | 41 | 14 | 12 | 7 | 9 | 9 |
| 66 | INFA 10e1 #3 | 23 | 37 | 12 | 28 | 23 | 13 | 40 | 12 | 16 | 11 | 17 | 19 |
| 67 | INFB 10e4 ctrl | 17 | 24 | 11 | 35 | 349 | 14 | 47 | 10 | 10 | 13 | 13 | 8 |
| 68 | INFB 10e4 #1 | 11 | 32 | 10 | 36 | 174 | 21 | 40 | 13 | 8 | 12 | 14 | 19 |
| 69 | INFB 10e4 #2 | 12 | 30 | 5 | 32 | 266 | 19 | 56 | 10 | 11 | 9 | 8 | 4 |
| 70 | INFB 10e4 #3 | 13 | 28 | 13 | 26 | 277 | 20 | 53 | 12 | 15 | 15 | 13 | 12 |
| 71 | INFB 10e3 #1 | 13 | 31 | 15 | 20 | 20 | 16 | 61 | 14 | 12 | 15 | 10 | 10 |
| 72 | INFB 10e3 #2 | 10 | 30 | 11 | 22 | 20 | 19 | 43 | 13 | 12 | 6 | 12 | 6 |
| 73 | INFB 10e3 #3 | 16 | 35 | 14 | 29 | 31 | 22 | 53 | 9 | 2 | 15 | 16 | 13 |
| 74 | INFB 10e2 #1 | 12 | 29 | 11 | 24 | 33 | 17 | 50 | 16 | 12 | 6 | 13 | 18 |
| 75 | INFB 10e2 #2 | 15 | 28 | 8 | 19 | 22 | 19 | 65 | 15 | 11 | 16 | 17 | 13 |
| 76 | INFB 10e2 #3 | 20 | 38 | 18 | 31 | 23 | 17 | 67 | 8 | 12 | 5 | 11 | 16 |
| 77 | INFB 10e1 #1 | 11 | 35 | 7 | 30 | 44 | 12 | 76 | 8 | 18 | 5 | 9 | 14 |
| 78 | INFB 10e1 #2 | 19 | 44 | 13 | 28 | 42 | 14 | 96 | 13 | 2 | 8 | 12 | 7 |
| 79 | INFB 10e1 #3 | 18 | 30 | 4 | 28 | 25 | 17 | 69 | 13 | 6 | 3 | 16 | 14 |
| 80 | PIV-1 10e4 ctrl | 12 | 69 | 16 | 23 | 33 | 380 | 94 | 15 | 7 | 12 | 20 | 13 |
| 81 | PIV-1 10e4 #1 | 16 | 54 | 8 | 20 | 18 | 461 | 47 | 8 | 17 | 5 | 18 | 9 |
| 82 | PIV-1 10e4 #2 | 17 | 42 | 11 | 21 | 33 | 555 | 40 | 8 | 12 | 9 | 15 | 6 |
| 83 | PIV-1 10e4 #3 | 14 | 32 | 10 | 14 | 16 | 630 | 38 | 10 | 9 | 17 | 12 | 6 |
| 84 | PIV-1 10e3 #1 | 10 | 31 | 8 | 13 | 13 | 145 | 39 | 9 | 10 | 10 | 13 | 4 |
| 85 | PIV-1 10e3 #2 | 22 | 46 | 6 | 13 | 13 | 149 | 54 | 13 | 19 | 11 | 13 | 16 |
| 86 | PIV-1 10e3 #3 | 12 | 35 | 12 | 20 | 10 | 98 | 52 | 12 | 15 | 10 | 15 | 12 |
| 87 | PIV-1 10e2 #1 | 15 | 40 | 6 | 16 | 4 | 26 | 37 | 6 | 7 | 12 | 13 | 9 |
| 88 | PIV-1 10e2 #2 | 17 | 44 | 11 | 20 | 11 | 27 | 57 | 9 | 13 | 9 | 9 | 10 |

TABLE 8-continued

Table 4 The sensitivity of the assay system

| | Sample/Target | ADV | CPN | MPN | INFA | INFB | PIV1 | PIV3 | RSV | SARS1 | SARS2 | SARS3 | ENT |
|---|---|---|---|---|---|---|---|---|---|---|---|---|---|
| 89 | PIV-1 10e2 #3 | 22 | 38 | 13 | 18 | 10 | 35 | 57 | 12 | 9 | 9 | 18 | 9 |
| 90 | PIV-1 10e1 #1 | 14 | 41 | 16 | 22 | 13 | 19 | 56 | 16 | 13 | 3 | 10 | 9 |
| 91 | PIV-1 10e1 #2 | 9 | 46 | 14 | 24 | 14 | 10 | 45 | 10 | 11 | 13 | 13 | 13 |
| 92 | PIV-1 10e1 #3 | 9 | 41 | 5 | 11 | 18 | 33 | 53 | 15 | 10 | 13 | 12 | 11 |
| 93 | PIV-3 10e4 ctrl | 12 | 54 | 16 | 30 | 33 | 25 | 1341 | 16 | 11 | 15 | 13 | 15 |
| 94 | PIV-3 10e4 #1 | 12 | 58 | 5 | 29 | 18 | 31 | 290 | 21 | 8 | 7 | 11 | 5 |
| 95 | PIV-3 10e4 #2 | 22 | 62 | 20 | 42 | 22 | 33 | 272 | 14 | 20 | 15 | 20 | 25 |
| 96 | PIV-3 10e4 #3 | 13 | 49 | 8 | 30 | 16 | 21 | 229 | 13 | 7 | 0 | 10 | 21 |
| 97 | PIV-3 10e3 #1 | 17 | 67 | 9 | 34 | 13 | 14 | 214 | 15 | 8 | 18 | 12 | 17 |
| 98 | PIV-3 10e3 #2 | 18 | 70 | 15 | 39 | 13 | 21 | 301 | 11 | 9 | 7 | 11 | 11 |
| 99 | PIV-3 10e3 #3 | 12 | 64 | 21 | 40 | 10 | 32 | 265 | 15 | 11 | 18 | 15 | 23 |
| 100 | PIV-3 10e2 #1 | 17 | 67 | 16 | 23 | 4 | 29 | 171 | 15 | 20 | 10 | 17 | 7 |
| 101 | PIV-3 10e2 #2 | 21 | 67 | 8 | 31 | 11 | 21 | 189 | 13 | 21 | 6 | 17 | 6 |
| 102 | PIV-3 10e2 #3 | 16 | 67 | 9 | 36 | 10 | 36 | 181 | 19 | 10 | 13 | 9 | 15 |
| 103 | PIV-3 10e1 #1 | 12 | 76 | 14 | 34 | 15 | 30 | 190 | 8 | 12 | 10 | 9 | 11 |
| 104 | PIV-3 10e1 #2 | 13 | 70 | 14 | 32 | 14 | 35 | 215 | 21 | 4 | 8 | 11 | 15 |
| 105 | PIV-3 10e1 #3 | 19 | 26 | 13 | 32 | 18 | 33 | 36 | 13 | 11 | 10 | 19 | 12 |
| 106 | RSVB 10e4 ctrl | 19 | 47 | 7 | 16 | 25 | 16 | 82 | 1232 | 11 | 9 | 15 | 18 |
| 107 | RSVB 10e4 #1 | 11 | 47 | 16 | 32 | 31 | 18 | 93 | 1154 | 7 | 9 | 11 | 24 |
| 108 | RSVB 10e4 #2 | 13 | 48 | 14 | 25 | 33 | 22 | 91 | 905 | 10 | 9 | 12 | 16 |
| 109 | RSVB 10e4 #3 | 13 | 39 | 14 | 25 | 21 | 21 | 76 | 948 | 5 | 8 | 9 | 15 |
| 110 | RSVB 10e3 #1 | 6 | 38 | 17 | 28 | 14 | 26 | 73 | 149 | 19 | 17 | 15 | 20 |
| 111 | RSVB 10e3 #2 | 16 | 42 | 6 | 21 | 21 | 20 | 76 | 217 | 11 | 15 | 19 | 16 |
| 112 | RSVB 10e3 #3 | 14 | 42 | 8 | 29 | 32 | 28 | 84 | 198 | 6 | 9 | 12 | 24 |
| 113 | RSVB 10e2 #1 | 11 | 44 | 16 | 33 | 29 | 17 | 100 | 40 | 14 | 16 | 7 | 21 |
| 114 | RSVB 10e2 #2 | 6 | 39 | 16 | 23 | 21 | 21 | 88 | 23 | 15 | 9 | 11 | 14 |
| 115 | RSVB 10e2 #3 | 20 | 41 | 12 | 20 | 36 | 22 | 90 | 29 | 9 | 17 | 13 | 25 |
| 116 | RSVB 10e1 #1 | 23 | 49 | 10 | 29 | 30 | 18 | 95 | 12 | 16 | 11 | 7 | 17 |
| 117 | RSVB 10e1 #2 | 15 | 44 | 15 | 27 | 35 | 17 | 94 | 11 | 11 | 7 | 5 | 18 |
| 118 | RSVB 10e1 #3 | 13 | 54 | 20 | 35 | 33 | 24 | 91 | 23 | 10 | 16 | 9 | 16 |
| 119 | SARS 10e4 ctrl | 34 | 34 | 13 | 14 | 33 | 27 | 34 | 15 | 212 | 1686 | 334 | 19 |
| 120 | SARS 10e4 #1 | 33 | 29 | 12 | 18 | 36 | 19 | 30 | 17 | 2066 | 1742 | 337 | 14 |
| 121 | SARS 10e4 #2 | 36 | 27 | 15 | 21 | 32 | 29 | 31 | 18 | 1514 | 1438 | 274 | 18 |
| 122 | SARS 10e3 #1 | 44 | 37 | 16 | 17 | 31 | 33 | 31 | 20 | 1245 | 1316 | 252 | 13 |
| 123 | SARS 10e3 #2 | 27 | 28 | 14 | 14 | 24 | 25 | 33 | 17 | 930 | 1069 | 180 | 11 |
| 124 | SARS 10e2 #1 | 53 | 27 | 17 | 13 | 20 | 28 | 30 | 17 | 479 | 664 | 119 | 12 |
| 125 | SARS 10e2 #2 | 42 | 24 | 13 | 21 | 17 | 27 | 29 | 15 | 196 | 381 | 53 | 9 |
| 126 | SARS 10e1 #1 | 46 | 22 | 8 | 17 | 17 | 24 | 36 | 15 | 88 | 168 | 37 | 15 |
| 127 | SARS 10e1 #2 | 10 | 16 | 14 | 23 | 10 | 17 | 28 | 10 | 6 | 4 | 5 | 18 |
| 128 | RhV 10e4 ctrl | 7 | 31 | 10 | 22 | 25 | 19 | 76 | 10 | 10 | 9 | 9 | 838 |
| 129 | RhV 10e3 #1 | 11 | 29 | 11 | 32 | 25 | 16 | 83 | 11 | 9 | 10 | 14 | 737 |
| 130 | RhV 10e3 #2 | 11 | 29 | 3 | 27 | 18 | 10 | 69 | 11 | 10 | 4 | 8 | 835 |
| 131 | RhV 10e3 #3 | 13 | 32 | 9 | 25 | 16 | 17 | 66 | 15 | 6 | 7 | 9 | 775 |
| 132 | RhV 10e2 #1 | 9 | 35 | 12 | 15 | 12 | 18 | 56 | 10 | 6 | 7 | 9 | 116 |
| 133 | RhV 10e2 #2 | 11 | 33 | 11 | 25 | 12 | 14 | 58 | 7 | 14 | 8 | 6 | 133 |
| 134 | RhV 10e2 #3 | 14 | 23 | 12 | 16 | 14 | 23 | 60 | 11 | 11 | 9 | 4 | 104 |
| 135 | RhV 10e1 #1 | 14 | 31 | 22 | 20 | 21 | 22 | 58 | 12 | 13 | 11 | 8 | 23 |
| 136 | RhV 10e1 #2 | 5 | 36 | 17 | 27 | 22 | 22 | 69 | 11 | 5 | 8 | 9 | 22 |
| 137 | RhV 10e1 #3 | 14 | 28 | 11 | 24 | 17 | 23 | 59 | 13 | 8 | 10 | 15 | 16 |
| 138 | CVA 10e4 ctrl | 16 | 10 | 6 | 8 | 12 | 16 | 15 | 4 | 12 | 5 | 11 | 1837 |
| 139 | CVA 10e4 #1 | 8 | 22 | 10 | 17 | 12 | 10 | 20 | 10 | 5 | 5 | 9 | 1285 |
| 140 | CVA 10e4 #2 | 9 | 22 | 6 | 16 | 7 | 16 | 27 | 7 | 10 | 5 | 10 | 1288 |
| 141 | CVA 10e4 #3 | 4 | 20 | 12 | 30 | 9 | 12 | 20 | 5 | 7 | 7 | 9 | 966 |
| 142 | CVA 10e3 #1 | 7 | 30 | 12 | 23 | 30 | 15 | 73 | 12 | 11 | 10 | 10 | 146 |
| 143 | CVA 10e3 #2 | 1 | 31 | 9 | 19 | 25 | 12 | 61 | 14 | 0 | 5 | 6 | 149 |
| 144 | CVA 10e3 #3 | 10 | 40 | 9 | 16 | 22 | 10 | 65 | 5 | 4 | 6 | 3 | 194 |
| 145 | CVA 10e2 #1 | 4 | 16 | 8 | 14 | 9 | 16 | 32 | 14 | 5 | 3 | 5 | 18 |
| 146 | CVA 10e2 #2 | 10 | 26 | 5 | 21 | 11 | 9 | 38 | 7 | 7 | 11 | 5 | 86 |
| 147 | CVA 10e2 #3 | 14 | 21 | 6 | 16 | 17 | 11 | 35 | 14 | 2 | 8 | 11 | 16 |
| 148 | CVA 10e1 #1 | 9 | 21 | 5 | 21 | 12 | 16 | 31 | 3 | 2 | 5 | 9 | 9 |
| 149 | CVA 10e1 #2 | 9 | 33 | 13 | 15 | 11 | 18 | 43 | 6 | 11 | 10 | 6 | 9 |
| 150 | CVA 10e1 #3 | 11 | 30 | 6 | 18 | 26 | 16 | 58 | 10 | 8 | 9 | 5 | 20 |
| 151 | CVB 10e4 ctrl | 9 | 15 | 6 | 10 | 8 | 13 | 18 | 11 | 12 | 10 | 14 | 2117 |
| 152 | CVB 10e4 #1 | 8 | 30 | 4 | 25 | 26 | 12 | 41 | 2 | 2 | 11 | 12 | 515 |
| 153 | CVB 10e4 #2 | 9 | 26 | 8 | 13 | 21 | 16 | 33 | 6 | 6 | 6 | 5 | 395 |
| 154 | CVB 10e4 #3 | 13 | 30 | 9 | 12 | 10 | 13 | 38 | 8 | 9 | 5 | 8 | 144 |
| 155 | CVB 10e3 #1 | 6 | 23 | 15 | 24 | 21 | 15 | 37 | 9 | 8 | 8 | 11 | 106 |
| 156 | CVB 10e3 #2 | 10 | 23 | 6 | 20 | 12 | 8 | 23 | 11 | 2 | 0 | 6 | 14 |
| 157 | CVB 10e3 #3 | 12 | 22 | 7 | 28 | 13 | 7 | 34 | 16 | 6 | 4 | 10 | 84 |
| 158 | CVB 10e2 #1 | 9 | 23 | 2 | 16 | 10 | 6 | 29 | 8 | 5 | 6 | 10 | 20 |
| 159 | CVB 10e2 #2 | 11 | 27 | 5 | 17 | 15 | 23 | 26 | 17 | 12 | 12 | 9 | 20 |
| 160 | CVB 10e2 #3 | 4 | 21 | 13 | 16 | 9 | 13 | 28 | 12 | 12 | 6 | 12 | 8 |
| 161 | CVB 10e1 #1 | 5 | 24 | 5 | 8 | 12 | 16 | 18 | 7 | 9 | 8 | 9 | 2 |
| 162 | CVB 10e1 #2 | 10 | 16 | 14 | 23 | 10 | 17 | 28 | 10 | 6 | 4 | 5 | 7 |
| 163 | CVB 10e1 #3 | 15 | 18 | 10 | 21 | 15 | 17 | 29 | 8 | 2 | 11 | 10 | 8 |

TABLE 8-continued

Table 4 The sensitivity of the assay system

| Sample/Target | ADV | CPN | MPN | INFA | INFB | PIV1 | PIV3 | RSV | SARS1 | SARS2 | SARS3 | ENT |
|---|---|---|---|---|---|---|---|---|---|---|---|---|
| mean of background | 14.2 | 36.2 | 11.3 | 24.8 | 20.5 | 19.1 | 60.9 | 12.2 | 9.9 | 9.5 | 11.4 | 13.7 |
| Standard deviation | 7.9 | 12.7 | 4.4 | 7.5 | 9.0 | 6.3 | 23.9 | 4.2 | 4.5 | 4.1 | 4.0 | 6.4 |
| Cutoff | 53.5 | 99.5 | 33.6 | 62.2 | 65.7 | 50.9 | 180.2 | 32.9 | 32.4 | 30.0 | 31.5 | 45.7 |

TABLE 9

| Sample | SARS1 | SARS2 | SARS4 | RSVA | RSVB | PIV-1 | PIV-3 | INFA | INFB | MPN | CPN | CVEV | ADV 3-7-21 | ADV 4 | ADV 14 |
|---|---|---|---|---|---|---|---|---|---|---|---|---|---|---|---|
| SARS | 688 | 614 | 183 | 6 | 11 | 12 | 0 | 22 | 10 | 0 | 7 | 3 | 12 | 4 | 9 |
| RSVA | 25 | 39 | 17 | 3388 | 24 | 33 | 11 | 12 | 18 | 32 | 21 | 34 | 71 | 24 | 15 |
| RSVB | 13 | 19 | 27 | 20 | 2538 | 18 | 8 | 29 | 25 | 27 | 25 | 26 | 43 | 22 | 6 |
| PIV-1 | 33 | 7 | 33 | 19 | 14 | 2008 | 19 | 23 | 13 | 19 | 28 | 23 | 13 | 19 | 5 |
| PIV-3 | 15 | 21 | 29 | 20 | 12 | 25 | 1189 | 14 | 22 | 22 | 29 | 24 | 49 | 15 | 22 |
| InfA | 29 | 29 | 29 | 8 | 19 | 39 | 29 | 759 | 19 | 27 | 28 | 19 | 34 | 9 | 19 |
| InfB | 17 | 22 | 15 | 19 | 11 | 35 | 11 | 34 | 795 | 11 | 32 | 14 | 20 | 19 | 22 |
| MPN | 7 | 25 | 31 | 20 | 31 | 22 | 18 | 29 | 27 | 2304 | 37 | 21 | 41 | 27 | 9 |
| CPN | 22 | 11 | 18 | 18 | 23 | 20 | 23 | 18 | 14 | 21 | 1626 | 34 | 32 | 22 | 3 |
| Sample Skipped | 9 | 28 | 16 | 31 | 17 | 30 | 17 | 16 | 14 | 11 | 28 | 25 | 26 | 8 | 11 |
| CVA-21 & EV-11 | 25 | 22 | 24 | 12 | 24 | 28 | 24 | 25 | 35 | 18 | 16 | 1376 | 32 | 5 | 15 |
| CVB-4 | 25 | 17 | 22 | 19 | 25 | 21 | 23 | 30 | 28 | 25 | 18 | 1276 | 28 | 24 | 12 |
| RhV | 32 | 23 | 29 | 18 | 14 | 35 | 28 | 18 | 21 | 32 | 27 | 18 | 24 | 36 | 20 |
| ADV 3 | 19 | 36 | 21 | 39 | 23 | 23 | 24 | 35 | 15 | 16 | 26 | 19 | 2458 | 15 | 88 |
| ADV 4 | 20 | 12 | 18 | 24 | 18 | 26 | 7 | 20 | 29 | 29 | 37 | 28 | 520 | 1242 | 26 |
| ADV 7 | 31 | 11 | 27 | 31 | 21 | 22 | 29 | 26 | 39 | 28 | 20 | 29 | 1758 | 21 | 28 |
| ADV 14 | 36 | 20 | 16 | 23 | 15 | 18 | 21 | 24 | 13 | 20 | 17 | 19 | 654 | 9 | 1697 |
| ADV 21 | 17 | 20 | 26 | 19 | 18 | 29 | 19 | 9 | 9 | 21 | 23 | 14 | 2235 | 15 | 90 |
| RT-PCR Blank 1 | 22 | 6 | 14 | 20 | 18 | 24 | 15 | 31 | 14 | 26 | 18 | 4 | 28 | 9 | 10 |
| RT-PCR Blank 2 | 15 | 13 | 30 | 6 | 17 | 7 | 27 | 23 | 9 | 6 | 24 | 24 | 13 | 2 | 15 |

What is claimed is:

1. A method for multiplex primer-based amplification of a target sequence from a plurality of agents, said target sequence being different for each agent, said method comprising:
   a. carrying out a first amplification reaction for each target sequence to be amplified using
      i) as a template, a nucleic acid from each of said plurality of agents, said nucleic acid containing said target sequence;
      ii) a first pair of target enrichment primers hybridizing to said nucleic acid and bracketing said target sequence;
      iii) a second pair of target enrichment primers hybridizing to said nucleic acid and bracketing said target sequence, said second pair of target enrichment primers being located proximate to said target sequence and one of the second pair of target enrichment primers comprising at its 5' end a binding tag corresponding to the sequence of one of a pair of target amplification primers and the other of the second pair of target enrichment primers comprising at its 5' end a binding tag corresponding to the sequence of the other of said pair of target amplification primers, wherein the second pair of target enrichment primers binds to the inside of the first set of target enrichment primers; and
      iv) amplification reagents and conditions for said first amplification reaction such that the first amplification reaction generates a plurality of first amplification products, wherein at least a portion of the first amplification products contain said target sequence and at least one complement of the binding tag for one of said target enrichment primers thereby forming at least one binding site for at least one of said target amplification primers; and
   b. carrying out a second amplification reaction for each target sequence to be amplified using
      i) as a template, said portion of the first amplification products containing said at least one binding site for at least one of said target amplification primers;
      ii) at least one of said first pair of target amplification primers binding to its corresponding binding sites on said portion of said first amplification products; and
      iii) amplification reagents and conditions for said second amplification reaction such that the second amplification reaction generates a plurality of second amplification products containing the target sequence.

2. The method of claim 1 where said first pair of target enrichment primers comprises a reverse outer ($R_o$) and a forward outer ($F_o$) primer, said second pair of target enrichment primers comprises a forward inner ($F_i$) and a reverse inner ($R_i$) primer and said first pair of target amplification primers comprises a forward super primer (FSP) and a reverse super primer (RSP).

3. The method of claim 2 where said binding tag on $F_i$ is identical to the sequence of the FSP such that the FSP binds the complement of the binding tag on said $F_i$ primer and the binding tag on $R_i$ is identical to the sequence of the RSP such that the RSP binds the complement of the binding tag on said $R_i$ primer.

4. The method of claim 1 where the length of each of the first pair of target enrichment primers is selected from the group consisting of: 10-40 nucleotides, 10-30 nucleotides and 10-20 nucleotides.

5. The method of claim 1 where the length of each of the second pair of target enrichment primers is selected from the group consisting of: 10-40 nucleotides, 10-30 nucleotides and 10-20 nucleotides.

6. The method of claim 1 where the length of each of the first pair of target enrichment primers is 10-20 nucleotides and the length of each of the second pair of target enrichment primers is 30 to 40 nucleotides.

7. The method of claim 1 where the length of each of the first pair of target amplification primers is 10-20 nucleotides and the length of each of the second pair of target enrichment primers is 30 to 40 nucleotides.

8. The method of claim 1 where the target enrichment primers are present at a low concentration and the target amplification primers are present at a high concentration.

9. The method of claim 8 where said low concentration is a concentration of 0.002 µM to 0.2 µM and said high concentration is a concentration of 0.2 µM to 1.0 µM.

10. The method of claim 1 where the target enrichment primers are present at a concentration that is not sufficient for exponential amplification of the target sequence and the target amplification primers are present at a concentration that is sufficient for exponential amplification of the target sequence.

11. The method of claim 1 where each of the target enrichment primers is used at the same concentration.

12. The method of claim 1 where at least one of the target enrichment primers is used at a higher concentration than the other target enrichment primers.

13. The method of claim 1 where each of the target amplification primers is used at the same concentration.

14. The method of claim 1 where at least one of the target amplification primers is used at a higher concentration than the other target amplification primer.

15. The method of claim 14 where said target amplification primer at said higher concentration comprises a means for detection.

16. The method of claim 1 where the conditions for said first amplification reaction comprise at least two complete cycles of a target enrichment process and the conditions for said second amplification reaction comprise at least two complete cycles of a target amplification process.

17. The method of claim 16 where the target enrichment process comprises the following conditions for amplification: 0.5 to 1 minute at 92-94° C., 1-2.5 minutes at 50-55° C. and 0.5 to 1 minute at 70-72° C. and the target amplification process comprises the following conditions for amplification: 15 to 30 seconds at 94° C., 15 to 30 seconds at 50-55° C. and 15 to 30 second at 72° C.

18. The method of claim 1 where the conditions for said first amplification reaction comprise at least two complete cycles of a target enrichment process and at least two complete cycles of a selective amplification process and the conditions for said second amplification reaction comprise at least two complete cycles of a target amplification process.

19. The method of claim 18 where the target enrichment process comprises the following conditions for amplification: 0.5 to 1 minute at 92-94° C., 1-2.5 minutes at 50-55° C. and 0.5 to 1 minute at 70-72° C., the selective amplification process comprises the following conditions for amplification: 15 to 30 seconds at 92-94° C., 1 to 2 minutes at 70-72° C. and the target amplification process comprises the following conditions for amplification: 15 to 30 seconds at 94° C., 15 to 30 seconds at 50-55° C. and 15 to 30 second at 72° C.

20. The method of claim 19 where the selective amplification is biased toward the production of first amplification products containing the binding site for at least one of said target amplification primers.

21. The method of claim 19 where the length of each of the first pair of target enrichment primers is 10-20 nucleotides and the length of each of the second pair of target enrichment primers is 30 to 40 nucleotides.

22. The method of claim 1 further comprising three or more pairs of target enrichment primers.

23. The method of claim 1 further comprising two or more pairs of target amplification primers.

24. The method of claim 1 where said agent is selected from the group consisting of: a virus and a bacteria.

25. The method of claim 24 where said bacteria is selected from the group consisting of: *Mycoplasma* species and *Chlamydia* species.

26. The method of claim 24 where said agent is selected by the appropriate design of the first and second pair of target enrichment primers.

27. The method of claim 24 where said virus is selected from the group consisting of: adenovirus, influenza A, influenza B, parainfluenza type 1, parainfluenza type 3, and respiratory syncytial virus, SARS, enterovirus, rhinovirus, and echovirus.

28. The method of claim 27 where said enterovirus is selected from the group consisting of: coxsackie virus A and coxsackie virus B.

29. The method of claim 1 where at least one of said target amplification primers further comprises a means for detection.

30. The method of claim 29 where said means for detection is selected from the group consisting of: a chemical element, an enzymatic element, a fluorescent element, or a radiolabel element.

31. The method of claim 1 further comprising detecting said target sequence.

32. The method of claim 31 where the detection method is a direct detection method.

33. The method of claim 31 where said detection method comprises:
   a. providing a detection oligonucleotide for each target sequence to be detected, each detection oligonucleotide comprising a first means for signal generation;
   b. contacting and incubating said detection oligonucleotide with said second amplification products;
   c. stimulating said first means for signal generation to produce a first signal; and
   d. detecting said first signal.

34. The method of claim 33 where said first signal is unique for each target sequence to be detected and said first signal is used to identify said agent.

35. The method of claim 33 where said means for first signal generation is a fluorescent label, a chemical label, an enzymatic label, or a radiolabel.

36. The method of claim 33 where said means for first signal generation is a fluorescent microsphere.

37. The method of claim 31 where said method is an indirect detection method.

38. A method of diagnosing the presence of a disease agent in a subject, said method comprising:
   a. providing a sample from said subject in need of said diagnosis, said sample suspected of containing said disease agent;
   b. isolating a nucleic acid from said sample, said nucleic acid containing a target sequence from said disease agent;
   c. subjecting said nucleic acid to the primer-based amplification method of claim 1;
   d. detecting said target sequence from said disease agent.

39. A method for differentially diagnosing the presence of a disease agent and a secondary disease agent in a subject, said method comprising:
   a. providing a sample from said subject in need of said diagnosis, said sample suspected of containing said disease agent or said secondary disease agent;
   b. isolating a nucleic acid from said sample, said nucleic acid containing a target sequence from said disease agent or secondary disease agent or both;
   c. subjecting said nucleic acid to the primer-based amplification method of claim 1;
   d. detecting said target sequence from said disease agent or secondary disease agent or both.

* * * * *